(12) United States Patent
Steffen et al.

(10) Patent No.: US 8,870,888 B2
(45) Date of Patent: Oct. 28, 2014

(54) BONE CEMENT INJECTION DEVICE

(76) Inventors: Thomas Steffen, Montreal (CA); Lorne Beckman, Montreal (CA); Demetrios Giannitsios, Edmonton (CA)

( * ) Notice: Subject to any disclaimer, the term of this patent is extended or adjusted under 35 U.S.C. 154(b) by 415 days.

(21) Appl. No.: 13/006,838

(22) Filed: Jan. 14, 2011

(65) Prior Publication Data

US 2011/0160737 A1    Jun. 30, 2011

Related U.S. Application Data

(63) Continuation of application No. PCT/CA2009/001002, filed on Jul. 15, 2009.

(60) Provisional application No. 61/080,808, filed on Jul. 15, 2008.

(51) Int. Cl.
*A61B 17/58* (2006.01)
*A61B 17/88* (2006.01)

(52) U.S. Cl.
CPC ......... *A61B 17/8822* (2013.01); *A61B 17/8827* (2013.01)
USPC .......................................................... 606/94

(58) Field of Classification Search
USPC ........ 606/92, 93, 94, 191, 201; 604/201–202, 604/204, 207, 212–213, 215, 236–238, 604/246–256; 251/149
See application file for complete search history.

(56) References Cited

U.S. PATENT DOCUMENTS

| | | | |
|---|---|---|---|
| 4,463,875 A * | 8/1984 | Tepic | ............................. 222/82 |
| 5,431,654 A | 7/1995 | Nic | |
| 5,514,135 A | 5/1996 | Earle | |
| 5,638,997 A | 6/1997 | Hawkins et al. | |
| 6,126,682 A | 10/2000 | Sharkey | |
| 6,348,055 B1 | 2/2002 | Preissman | |

(Continued)

FOREIGN PATENT DOCUMENTS

| | | | | |
|---|---|---|---|---|
| CA | 2435045 A1 | | 1/2004 | |
| CA | WO2007/028253 | * | 3/2007 | ............... A61M 5/00 |

(Continued)

OTHER PUBLICATIONS

International Search Report and Written Opinion for International Application No. PCT/CA2009/001002, mailed Oct. 21, 2009.

(Continued)

*Primary Examiner* — Nicholas Woodall
(74) *Attorney, Agent, or Firm* — Norton Rose Fulbright Canada LLP

(57) ABSTRACT

A system for injecting an incompressible low viscosity fluid into a bone cement reservoir adapted to be engaged with a cannula through which a high viscosity bone cement is transferred from the bone cement reservoir to a bone element is provided. The system comprises a control handle having a cylindrical body, a grip portion at an outer end of the cylindrical body and a central thumb-actuated plunger of a power piston, the grip portion being configured for receiving at least two fingers a user such as to permit actuation of the control handle by the single hand of the user, the cylindrical body including the power piston and a low viscosity fluid reservoir concentrically disposed relative to each other, the low viscosity fluid reservoir containing the incompressible low viscosity fluid and the power piston extending longitudinally through a center of the low viscosity fluid reservoir.

42 Claims, 17 Drawing Sheets

(56) References Cited

U.S. PATENT DOCUMENTS

| | | |
|---|---|---|
| 6,406,175 B1 | 6/2002 | Marino |
| 6,425,897 B2 | 7/2002 | Overes et al. |
| 6,547,432 B2 | 4/2003 | Coffeen et al. |
| 6,974,247 B2 | 12/2005 | Frei et al. |
| 7,008,433 B2 | 3/2006 | Voellmicke et al. |
| 7,112,205 B2 | 9/2006 | Carrison |
| 7,371,241 B2 | 5/2008 | Evans et al. |
| 7,393,342 B2 | 7/2008 | Henniges et al. |
| 7,524,103 B2 | 4/2009 | McGill et al. |
| 7,922,690 B2 | 4/2011 | Plishka et al. |
| 8,070,728 B2 | 12/2011 | Baroud |
| 8,235,256 B2 | 8/2012 | Green et al. |
| 8,246,628 B2 | 8/2012 | Rabiner |
| 8,257,310 B2 | 9/2012 | Donovan et al. |
| 8,333,773 B2 | 12/2012 | DiMauro et al. |
| 8,348,956 B2 | 1/2013 | Rabiner |
| 8,409,211 B2 | 4/2013 | Baroud |
| 2002/0099384 A1* | 7/2002 | Scribner et al. .................. 606/92 |
| 2003/0069545 A1* | 4/2003 | Arm .............................. 604/218 |
| 2004/0193171 A1 | 9/2004 | DiMauro et al. |
| 2005/0070915 A1 | 3/2005 | Mazzuca et al. |
| 2005/0113843 A1 | 5/2005 | Arramon |
| 2006/0133193 A1 | 6/2006 | Arramon |
| 2006/0264967 A1 | 11/2006 | Ferreyro et al. |
| 2007/0233146 A1 | 10/2007 | Henniges et al. |
| 2007/0233149 A1 | 10/2007 | Bohner et al. |
| 2008/0039856 A1 | 2/2008 | DiMauro |
| 2008/0195114 A1 | 8/2008 | Murphy |
| 2008/0243129 A1 | 10/2008 | Steffen |
| 2008/0255571 A1 | 10/2008 | Truckai et al. |
| 2009/0264942 A1 | 10/2009 | Beyar |
| 2009/0270872 A1 | 10/2009 | DiMauro |
| 2009/0292290 A1* | 11/2009 | Truckai et al. .................. 606/94 |
| 2010/0087828 A1 | 4/2010 | Krueger et al. |
| 2010/0114174 A1 | 5/2010 | Jones et al. |
| 2010/0274080 A1 | 10/2010 | Donovan et al. |
| 2010/0274255 A1 | 10/2010 | Donovan et al. |
| 2011/0015641 A1 | 1/2011 | Matsumoto |
| 2011/0112543 A1 | 5/2011 | Palazzolo |

FOREIGN PATENT DOCUMENTS

| | | |
|---|---|---|
| CN | 1950041 A | 4/2007 |
| EP | 0235905 A1 | 9/1987 |
| WO | 9728835 A1 | 8/1997 |
| WO | 2004080357 A1 | 9/2004 |
| WO | 2007028253 A2 | 3/2007 |

OTHER PUBLICATIONS

The State Intellectual Property Office of the People's Republic of China—Patent Search Report, mailed Sep. 24, 2012.

* cited by examiner

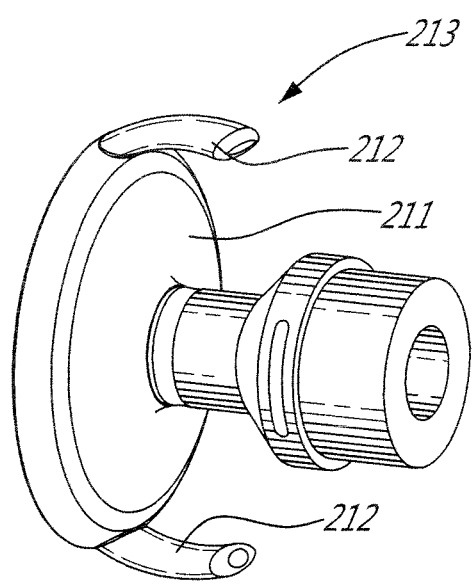

BONE CEMENT INJECTION DEVICE

CROSS-REFERENCE TO RELATED APPLICATIONS

The present application is a continuation of Intentional Patent Application No. PCT/CA2009/001002 filed Jul. 15, 2009, which claims priority on U.S. Provisional Patent Application No. 61/080,808 filed Jul. 15, 2008, the entire contents of both of which are incorporated herein by reference.

TECHNICAL FIELD

The present invention relates to the field of injection biomechanics, and more particularly to a system for injecting a high viscosity material, such as bone cement, to a bone site, for example vertebral bodies.

BACKGROUND OF THE ART

Percutaneous vertebroplasty is now commonly used to repair vertebrae which have become damaged or weakened, for example by osteoporosis, osteolytic spinal tumours, and the like. The gradual loss of bone minerals and progressive structural change of the trabecular bone which occur in osteoporosis result in vertebral fragility fractures. Vertebroplasty is used to improve the structural integrity of such mechanically weakened vertebrae affected by osteoporosis or tumors. This procedure involves the injection of viscous bone cement into the trabecular bone of the vertebral body. The bone cement, once hardened, becomes a permanent reinforcement of the vertebral body and usually drastically diminishes the pain experienced by the patient.

Transpedicular vertebroplasty is the most commonly used approach to access the vertebral body, however other approaches are also known, such as posterolateral and intertransverse. Transpedicular vertebroplasty involves the insertion of a cannula through the patient's skin, through the pedicle of the vertebra, and into the vertebral body. The vertebral body is then filled with bone cement, fed through the cannula, which solidifies within the vertebral body thereby stabilizing and strengthening the damaged vertebra.

Much of the equipment used to date for transpedicular vertebroplasty has been "off the shelf" surgical tools, which were originally designed for other procedures but which has been adapted for use with this procedure. As a result, the transpedicular vertebroplasty procedure itself has not to date been optimized, such as to improve the ease of performing this surgical procedure while reducing the risk to both patient and surgeon.

Further, improvement is sought for several different aspects of current equipment used for transpedicular vertebroplasty. For example, one risk inherent with the transpedicular vertebroplasty is the potential for bone cement leakage out of the vertebral body and into the venous system or into the spinal canal, which can cause serious, life threatening complications. Many of the more recent attempts to provide improvements have been focused on this point. The bone cement is believed to leak because it is injected at a low viscous or liquid like state. While increasing the viscosity of the bone cement injection has been associated with fewer leaks, thereby improving the safety of the procedure, a large injection force is required in order to be able to generate a pressure which is sufficiently high to displace the cement. To generate these pressures, some clinicians have resorted to using small volume syringes (ex: 1 cc to 3 cc) to inject bone cement, because the smaller cross sectional area of such small syringes permits generating higher pressure to displace the higher viscosity bone cement which can still be generated by the surgeon using a one-handed pincer grip. The inherent disadvantage of such smaller syringes is that many are required to inject the recommended amount of cement into a single vertebral body (typically 6-8 cc in the lumbar region, maximum 10 cc). Also, small syringes lack the volumetric stiffness and strength of components (e.g., the plunger) to handle sufficiently high pressures (3-5 MPa and higher). The use of several small syringes is therefore time consuming and less than ideal. Filling and using multiple syringes requires the clinician to repeatedly change syringes, which can distract attention away from the procedure at hand and any potentially dangerous complications which may occur, such as leakage of the cement for example. Still other disadvantages of working with multiple small syringes are that the procedure is time consuming, messy, and filling multiple small syringes ahead of time with cement may cause the syringe nozzle to clog.

Several different prior art methods and devices exist, all of which attempt to solve this problem (i.e. the generation of sufficient pressure to be able to inject bone cements having higher viscosities), however all have disadvantages. For example, some such devices are large and bulky, and employ large hand lever pumps or power screws to displace the cement. The significant weight and bulk of such devices makes them less practical and unsuitable for mounting directly atop a bone biopsy cannula, because the weight may bend the cannula and fracture the osteoporotic pedicle. As a result, these devices must be connected to the cannula via a long, small diameter tubing. Long tubing is also used to connect the injection device with the cannula to avoid radiation that the surgeon's hand may otherwise be exposed to when manipulating the device in the radiation field of a fluoroscope. Fluoroscopes are routinely used for cement injection into vertebra, with the intent being to immediately visualize adverse cement flow. Unfortunately, the friction of the cement flowing through such a long small diameter tube is extremely high and, as a result, almost all of the force generated by the gun, pump or power screw is used to overcome this friction within the piping. Further, these large systems dramatically limit the tactile feel of the surgeon and their sheer size become very cumbersome and expensive when three or four units are required for use simultaneously, such as during a multi-segmental procedure.

Another challenge facing surgeons performing vertebroplasty is the determination of when the bone cement is ready to be injected into the vertebral body. The surgeon must therefore decide when the cement has reached an acceptable level of polymerization to permit safe injection thereof. This is often done by simply extruding a small sample of the cement from the end of the injector being used, and the surgeon manually determines based on the tactile feel of the material whether it "feels doughy". This method is clearly subjective, and further the sample taken may not be representative of the remaining cement in the injector, which may potentially be polymerizing at a different rate depending on a number of factors, including for example the thermal transfer properties of the reservoir material, room temperature and humidity, and the heat transferred from the hand of the surgeon to the sample as it is mechanically massaged.

Governmental organizations have also recently begun issuing notices to hospitals within their jurisdictions related to safety information on the use of bone cements, particularly for vertebroplasty and kyphoplasty operations. Accordingly, it is becoming increasingly important for surgeons to be able to accurately, effectively and safely inject bone cement, and thus continued improvement for devices employed to inject bone cement, and particularly high viscosity bone cement, is desired.

Some attempts at developing improved devices for the injection of high viscosity bone cement have been made. However, improvements continue to be sought, both in the design of the injector device itself as well as the entire system employed therewith for injecting high viscosity bone cement into patients, such as may be used, for example, when performing percutaneous vertebroplasty and/or other procedures used to improve the structural integrity of a given bone element.

SUMMARY OF THE INVENTION

It is therefore an aim of the present invention to provide an improved system and/or method for injecting high viscosity material, such as bone cement.

It is also an aim of the present invention to provide a device and method for injecting high viscosity material through a cannula into a bone site, such as into vertebral bodies for example.

Therefore, in accordance with one aspect of the present invention, there is provided a system for injecting an incompressible low viscosity fluid into a bone cement reservoir adapted to be engaged with a cannula through which a high viscosity bone cement is transferred from the bone cement reservoir to a bone element, the system comprising a control handle having a cylindrical body, a grip portion at an outer end of the cylindrical body and a central thumb-actuated plunger of a power piston, the grip portion being configured for receiving at least two fingers a user such as to permit actuation of the control handle by the single hand of the user, the cylindrical body including the power piston and a low viscosity fluid reservoir concentrically disposed relative to each other, the low viscosity fluid reservoir containing the incompressible low viscosity fluid and the power piston extending longitudinally through a center of the low viscosity fluid reservoir, the power piston having an inlet thereto in communication with the low viscosity fluid reservoir for drawing the low viscosity fluid into the power piston, and an outlet through which the low viscosity fluid is expelled when the plunger of the power piston is depressed by the thumb of the user.

In accordance with another aspect of the present invention, there is provided a system for injecting a high viscosity bone cement into a cannula for delivery to a bone element, comprising: a control handle configured for actuation by a single hand of a user, the control handle having a cylindrical body having a power piston and a low viscosity fluid reservoir concentrically disposed relative to each other, the low viscosity fluid reservoir containing an incompressible low viscosity fluid and the power piston extending longitudinally through a center of the low viscosity fluid reservoir, the power piston having an inlet thereto in communication with the low viscosity fluid reservoir for drawing the low viscosity fluid into the power piston, and an outlet through which the low viscosity fluid is expelled when a plunger of the power piston is depressed by the user; and a bone cement reservoir containing the high viscosity bone cement, the bone cement reservoir being remote from the control handle and connected thereto in fluid flow communication by an extension tube, having an inlet connected in fluid flow communication with the outlet of the power piston of the control handle and an outlet adapted to communicate with the cannula for transferring the high viscosity material thereto, the second reservoir having a non-compliant body defining a cavity therein, a diaphragm disposed within the cavity and having an outer periphery thereof fixed to the body, the diaphragm separating said cavity into a low viscosity fluid receiving portion on one side thereof and a high viscosity fluid receiving portion on the opposite side thereof, the low viscosity fluid receiving portion being in fluid communication with said inlet to the second reservoir and the high viscosity fluid receiving portion being in fluid communication with said outlet of the second reservoir, the diaphragm having a shape corresponding to opposed proximal and distal end walls of said cavity, the diaphragm being displaceable by the low viscosity fluid between a loaded position, wherein the diaphragm is abutted against the proximal end wall and the cavity is filled with said high viscosity material, and a dispensed position, wherein the diaphragm displaced towards the distal end wall and the cavity is at least partially filled with said low viscosity fluid, the diaphragm thereby being a material-moving membrane which is displaced by the low viscosity fluid acting thereagainst to force the high viscosity material on the opposite side of the diaphragm out of said cavity, via said outlet of the second reservoir, and into the cannula.

In accordance with another aspect of the present invention, there is provided a device for injecting high viscosity material into a bone element, comprising: a reservoir for storing the high viscosity material prior to injection thereof, the reservoir having a substantially non-compliant body defining a cavity therein, and including an inlet and outlet to said cavity, a material-moving membrane separating the cavity into a first portion having a first volume adapted to receive an incompressible low viscosity fluid via said inlet to said cavity and a second portion having a second volume adapted to receive the high viscosity material, the material-moving membrane being flexible such as to corresponding to opposed proximal and distal end walls of said cavity, the material-moving membrane being displaceable by the low viscosity fluid between a loaded position, wherein the material-moving membrane is abutted against the proximal end wall and the cavity contains only said high viscosity material therein, and a dispensed position, wherein the diaphragm is displaced towards the distal end wall by the low viscosity fluid, the material-moving membrane thereby varying the first and second volumes inversely proportionally; and a fluid injector connected in fluid flow communication with the inlet of the cavity, the fluid injector being actuable to displace the incompressible low viscosity fluid into the first portion of said cavity in order to displace the material-moving membrane therein to increase the first volume and decrease the second volume, thereby ejecting the high viscosity material out of the body via the outlet of the cavity.

In accordance with another aspect of the present invention, there is provided a cannula for delivery of a high viscosity material into a bone element, the cannula comprising: a tubular cannula body, the tubular cannula body defining a longitudinal axis and a conduit extending a length of the cannula body between an inlet and an outlet of the cannula, the conduit being adapted to receive the high viscosity material for delivery to said outlet; and a handle fixed to an outer end of the tubular cannula body proximate said inlet, the handle defining a length between two opposed ends thereof and a midpoint along said length, the handle extending substantially transversely relative to the longitudinal axis of the tubular cannula body, and the handle intersecting the tubular cannula body at an offset point on said handle located between said midpoint and one of the two opposed ends.

There is also provided a system for injecting high viscosity material into a cannula for delivery to a bone element, comprising: a reservoir for storing the high viscosity material prior to injection thereof, the reservoir having a substantially non-compliant body defining a cavity therein, and including an inlet and outlet to said cavity, a material-moving membrane separating the cavity into a first portion having a first volume adapted to receive an incompressible low viscosity fluid via said inlet to said cavity and a second portion having a second volume adapted to receive the high viscosity material, the material-moving membrane being displaceable by the low viscosity fluid between a loaded position, wherein the entire cavity is substantially filled with said high viscosity material, and a dispensed position, wherein the cavity is at substantially filled with said low viscosity fluid; a low viscosity fluid injector connected in fluid flow communication with the inlet of the reservoir, the fluid injector displacing the incompressible low viscosity fluid into the first portion of said cavity within said reservoir, thereby displacing the material-moving membrane therein to increase the first volume and decrease the second volume, thereby forcing the high viscosity material out of the body of said reservoir via said outlet; and a viscosity level indicator in heat transfer communication with at least the second portion of the cavity within said reservoir, the viscosity level indicator including a temperature sensor which continuously measures a temperature of the high viscosity fluid contained in said cavity, and an indicator element in electrical communication with said temperature sensor for indicating when the measured temperature reaches a predetermined rate of increase indicating that a threshold polymerization time of the high viscosity material has been reached, said threshold polymerization time corresponding to a selected viscosity level that is suitable for injection of the high viscosity material.

There is further provided a system for injecting a high viscosity material into a cannula for delivery to a patient site, comprising: a control handle configured for actuation by a single hand of a user and including a power piston concentrically disposed within a first reservoir containing an incompressible low viscosity fluid and extending longitudinally through the first reservoir, the power piston having an inlet thereto in communication with the first reservoir for drawing the low viscosity fluid therein, and an outlet through which the low viscosity fluid is displaced when a plunger of the power piston is depressed by the user; and a second reservoir having an inlet in fluid flow communication with the outlet of the power piston of the control handle and an outlet adapted to communicate with the cannula for transferring the high viscosity material thereto, the second reservoir having a non-compliant body defining a cavity therein, a diaphragm disposed within the cavity and having an outer periphery thereof fixed to the body, the diaphragm separating said cavity into a low viscosity fluid receiving portion on one side thereof and a high viscosity fluid receiving portion on the opposite side thereof, the low viscosity fluid receiving portion being in fluid communication with said inlet to the second reservoir and the high viscosity fluid receiving portion being in fluid communication with said outlet of the second reservoir, the diaphragm having a shape corresponding to opposed proximal and distal end walls of said cavity, the diaphragm being displaceable by the low viscosity fluid between a loaded position, wherein the diaphragm is abutted against the proximal end wall and the cavity is filled with said high viscosity material, and a dispensed position, wherein the diaphragm displaced towards the distal end wall and the cavity is at least partially filled with said low viscosity fluid, the diaphragm thereby being a material-moving membrane which is displaced by the low viscosity fluid acting thereagainst to force the high viscosity material on the opposite side of the diaphragm out of said cavity, via said outlet of the second reservoir, and into the cannula.

BRIEF DESCRIPTION OF THE DRAWINGS

Reference will now be made to the accompanying drawings, showing by way of illustration a preferred embodiment thereof, and in which:

FIG. 8b is a side view of the grip portion of FIG. 8a;

FIG. 8c is a perspective view of another alternate grip portion for the control handle of the present system;

DESCRIPTION OF THE PREFERRED EMBODIMENTS

Figure 1:
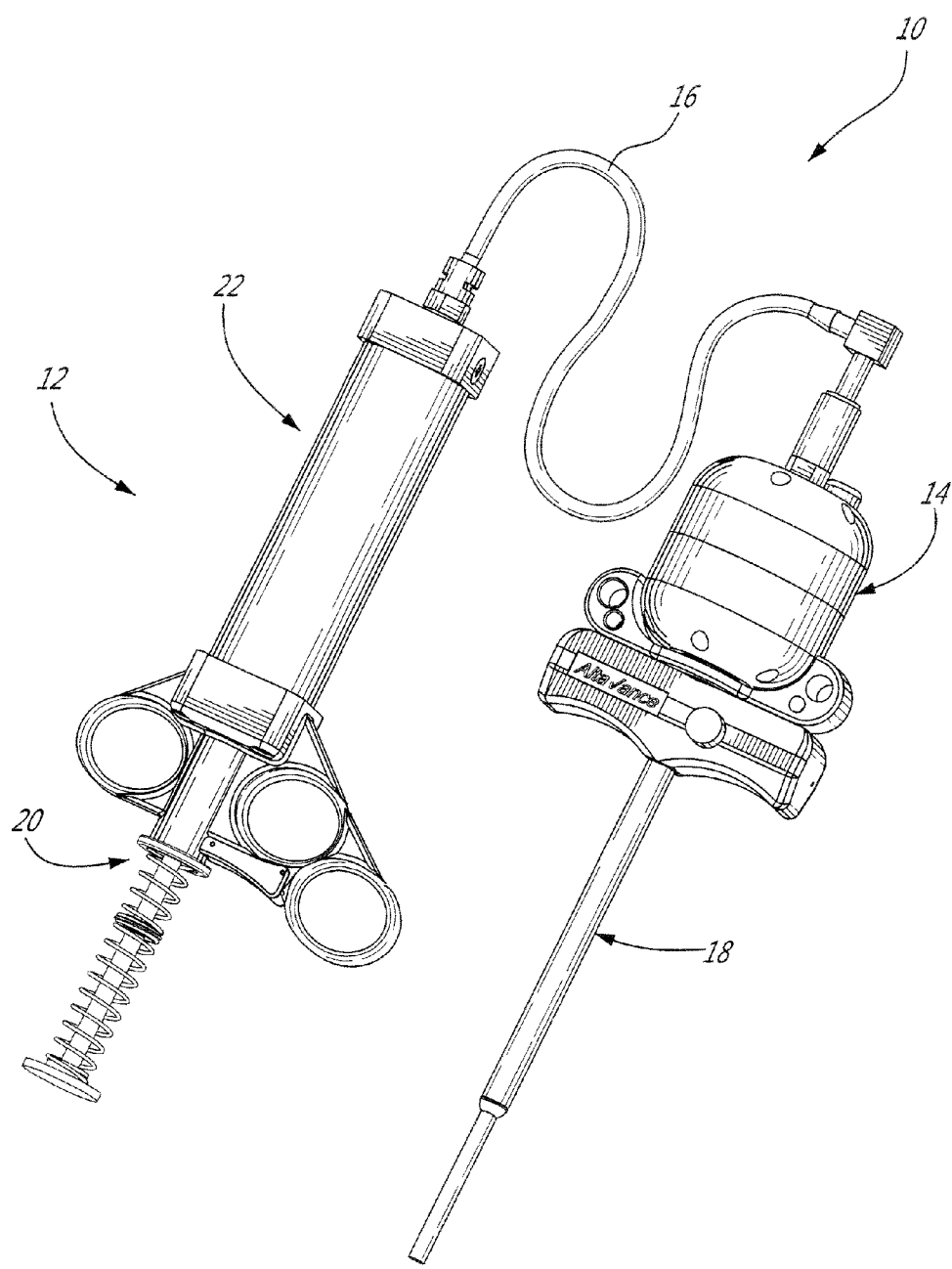
FIG. 1 is a perspective view of a first particular embodiment of the present bone cement injection system, the bone cement injection system including a cement reservoir mounted to a cannula, and a control handle interconnected with the cement reservoir by an extension tube.

The present injection system is preferably adapted for, and used to perform, percutaneous vertebroplasty and more particularly transpedicular vertebroplasty. However, the present system may also be adapted for other medical uses which involve injecting high viscosity material, either bone cement or otherwise, into a cavities, especially intraosseous ones.

Using the present injection system as described below, the vertebral body is filled with bone cement, such as Polymethyl Methacrylate [PMMA] for example, via a cannula and solidifies in and thus stabilizes the fractured vertebra. The cannula is inserted through the cutaneous layers and the cortical bone of the vertebra so that the tip of the cannula can be positioned transpedicularly in the cancellous bone of the vertebral body. The high viscosity bone cement is then able to be delivered through the cannula, usually under fluoroscopic guidance, into the trabecular bone of the vertebral body. By injecting the bone cement at a high viscosity, the likelihood of leaks is greatly reduced. However, as described above, challenges exist with being able to efficiently deliver a sufficient amount of high viscosity bone cement into the vertebral body. In order to uniformly infiltrate the vertebral body and avoid unwanted leakage, the bone cement preferably has a viscosity greater than 100 Pa*s, possibly even more than 300 Pa*s. The expression "viscous material" and/or "high viscosity" material is used herein to refer to a material having a viscosity significantly greater than that of the incompressible fluid, and preferably higher than 100 Pa*s, typically between 300 and 800 Pa*s, but potentially may be even much higher (up to 2,000 Pa*s). The viscous material can include, among other materials, Polymethyl Methacrylate (PMMA) cement, Calcium Phosphate cement, physical or chemical gels (e.g., Polyvinylalcohol, Polyurethane, or any number of other polymers or co-polymers). Although the term "bone cement" is used herein when referring to the present injection system and its components in order to simplify identification of the device and system (i.e. it is described herein often as a "bone cement injection system" or as having a "bone cement reservoir", for example), it is to be understood that the present system can be used to injection other high viscosity materials and thus is not limited to the injection of bone cement.

The design of the present bone cement injection system has been dramatically improved over the existing prior art systems, so as to make the device more user friendly, intuitive to use and safer, as a result of the reduced risk of bone cement leaks during surgery. The present system is capable of delivering bone cement having a greater viscosity than with other existing devices. Qualitatively, the present system is capable of delivering bone cement having a "pizza dough" consistency, whereas all other devices inject a bone cement having a "honey" like consistency. Furthermore, as will be described below, the present system significantly reduces the number of steps required to prepare the device and complete the bone cement injection into a bone element. A further advantage of the present system is the use of the change in bone cement temperature as an indicator that the viscosity of the bone cement is sufficiently high and therefore ready to be injected into the bone element.

The present injection system 10 improves upon certain prior devices for injecting high viscosity material, such as for example that described in International Patent Application Nos. PCT/CA2006/001487 filed Sep. 7, 2007 and PCT/CA2005/000222 filed Feb. 18, 2005, respectively published on Mar. 15, 2007 and Aug. 25, 2005 as International Patent Application Publication Nos. WO 2007/028253 and WO2005/077443, the entire contents of which are incorporated herein by reference.

Generally, the present system 10 is advantageous in that it provides sufficient mechanical advantage to the operator that high viscosity materials may be injected easily, while the device nonetheless remains small, compact and simple in design so that at least the bone cement reservoir can be mounted directly to a bone biopsy cannula. As noted below, part or all of the present system can be disposable after one use, so as to greatly simplify its use. As the bone cement reservoir is configured to be mounted directly to each cannula, this allows for the injection of multiple devices concurrently (e.g., during multilevel bone cement augmentation procedures in the spine). Alternatively, the cement reservoir can easily and quickly be switched between cannulae, so that a single reservoir can be used to deliver cement sequentially through multiple cannulae. Multiple cannulae may therefore be placed in the same vertebral body (paired left/right access), or in different vertebral bodies. In yet a different scenario, a number of bone cement reservoirs 14, as will be described in further detail below, can be mounted to their respective cannula, and the control handle portion 12 of the present system can be sequentially engaged to the each of the bone cement reservoirs for the injection of the bone cement contained therein. The present bone cement injection system is capable of generating mechanical advantage for injecting the high viscosity material into the patient. As noted below, some or all of the components of the present high viscosity material injection system may be disposable, further improving its safety and convenience of use.

Figure 2:
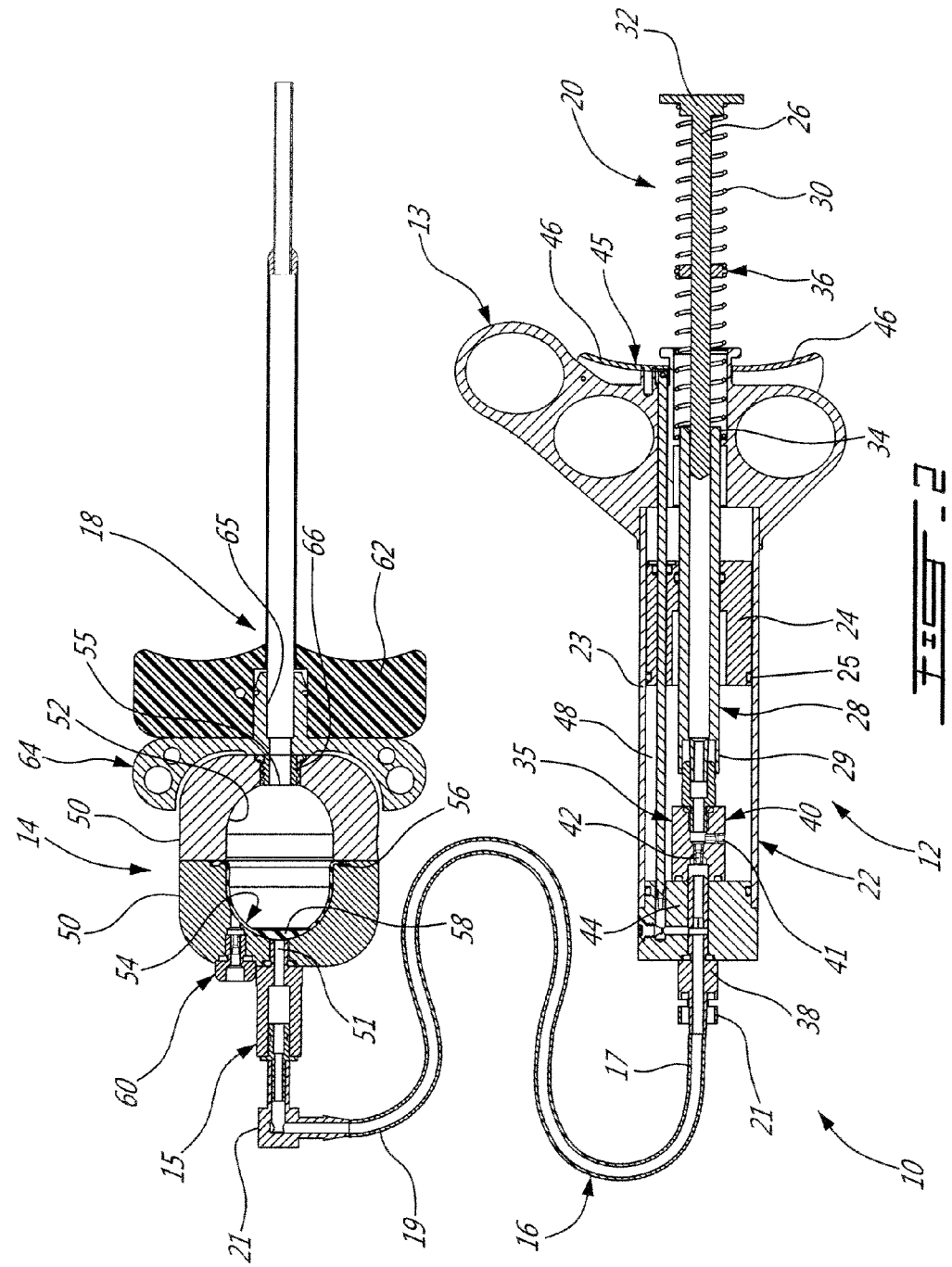
FIG. 2 is a detailed cross-sectional view of the bone cement injection system of FIG. 1.

Referring to FIGS. 1-2, the injection system 10 includes generally a fluid injector in the form of a control handle 12, a bone cement reservoir 14 and an extension tube 16 which interconnects the two in fluid flow communication. The general operation of the system is as follows. The fluid injector or control handle 12 is used to force a low viscosity fluid (LVF) out of a LVF reservoir within the control handle/fluid injector, through the extension tube 16 and into a cavity within the cement reservoir 14. As will be described in further detail, the LVF forced into the cement reservoir 14 by the fluid injector 12 displaces a similar quantity of high viscosity bone cement contained within an adjacent cavity of the cement reservoir, such that this quantity of bone cement is forced out of the bone cement reservoir 14, through the cannula 18 to which the reservoir is engaged in flow communication, and into the vertebral body or other bone element. As such, the system uses the easily displaced but incompressible LVF as a hydraulic fluid which forces the high viscosity bone cement out of the bone cement reservoir 14, through the cannula and into the injection site. As the bone cement reservoir 14 is mounted directly to the top of the cannula 18 in at least one possible embodiment (shown in FIGS. 1-2), the distance along which the high viscosity material (i.e. bone cement) is required to travel is minimized, thereby minimizing the friction resistance and thus the force required to be produced by the surgeon in order to deliver a complete quantity of the high viscosity material into the bone site with a single injection. The extension tube is preferably a thin and stiff tube (e.g., made of PEEK for example, and having a 1 mm inner diameter) having a desired length to operate the control handle conveniently outside the radiation field of the fluoroscope (e.g. 50 cm).

Each of the components of the injection system 10 will now be described in further detail, with reference to FIGS. 1-5. Each comprises specific innovative features which provide an improved overall system, both in terms of ease of use and improved tactile feel for the surgeon when injecting high viscosity bone cements, and in safety for the patient.

Figure 3:
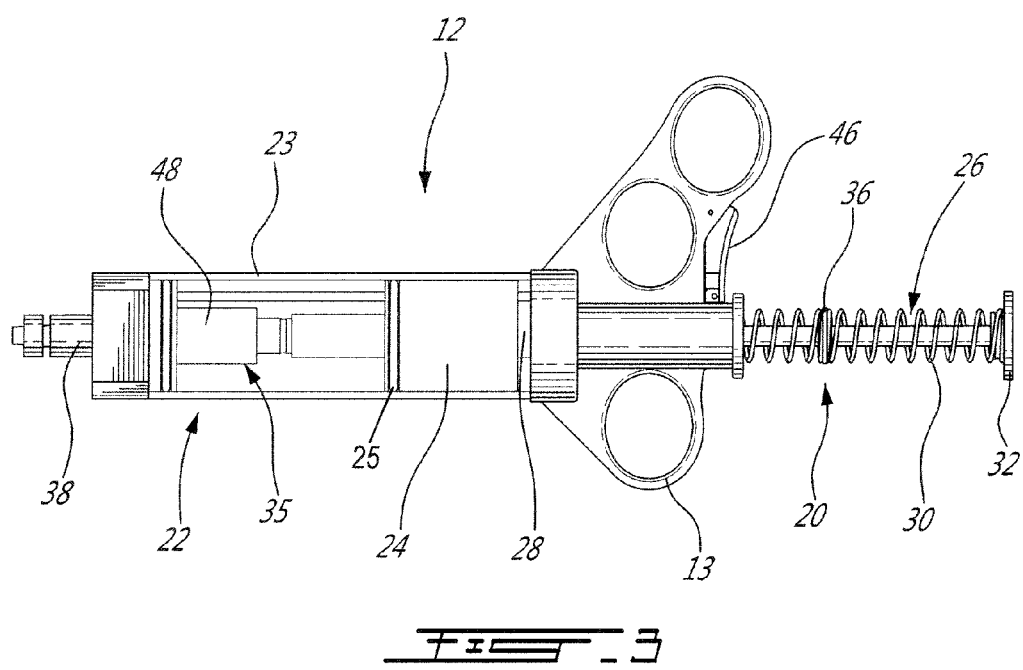
FIG. 3 is a side view of the control handle of the bone cement injection system of FIG. 1.

As best seen in FIGS. 2 and 3, the control handle 12 of the bone cement injection system 10 is made up generally of a power piston 20 and a low viscosity fluid (LVF) reservoir 22. The control handle includes a finger grip portion 13 which is mounted to the outer (or distal) end of the LVF reservoir 22 and designed for providing a comfortable grip of the control handle 12 by the surgeon with, for example, the three first fingers of the hand while permitting actuation of the plunger 26 of the power piston 20 with his or her thumb. Although the finger grip portion 13 shown in FIGS. 2-3 includes three finger "loops", which receive the surgeon's index, middle and ring fingers for example, other designs are also possible.

Figure 8B:
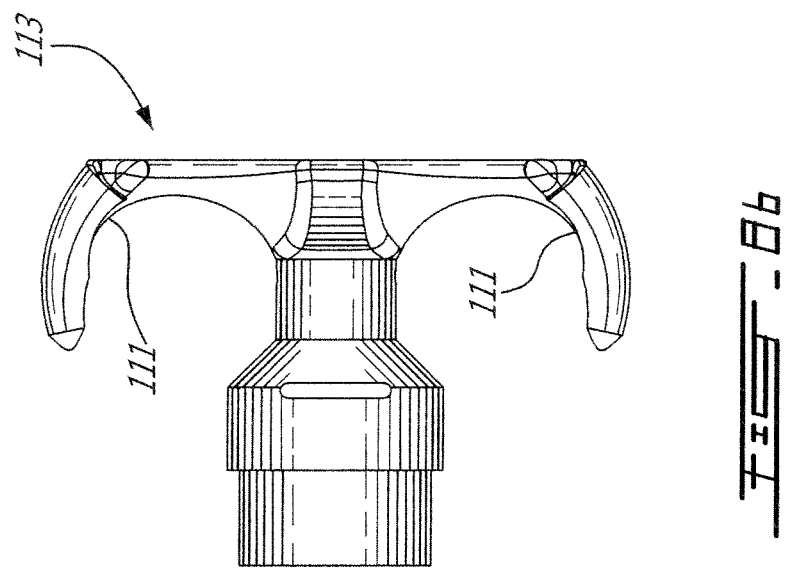
Figure 8A:
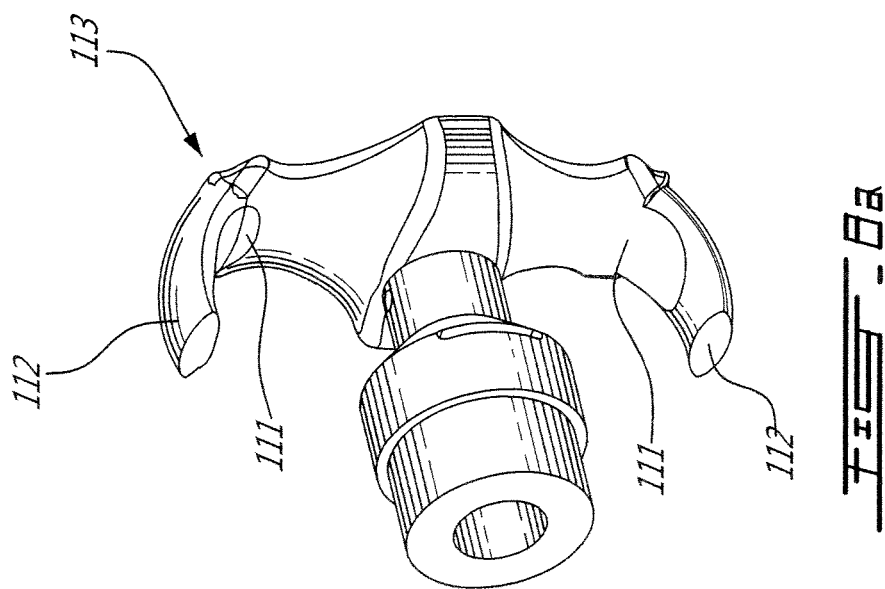
FIG. 8a is a perspective view of an alternate grip portion for the control handle of the present system.

For example, in an alternate embodiment as depicted in FIGS. 8a and 8b, the finger grip portion 113 includes only two finger grips are provided. The two opposed finger grips 111 of the finger grip portion 113 are also at least partially open, in that they do not form complete circular, enclosed finger loops which fully encircle the surgeon's fingers. Instead, the partially open finger grips 111 have a distal opening which allows the surgeon to grasp the control handle having such a grip portion 113 without needing to slide his fingers laterally through closed loop openings.

In yet a further alternate embodiment, shown in FIG. 8c, the finger grip portion 213 of the control handle comprises a single round disc or annular plate 211 which forms the grip portion 213 and permits sufficient control and manipulation of the control handle, with at least the surgeon's index and middle fingers for example, while still allowing for resistance during the depression of the plunger using a thumb. The round disc 211 has a concave distally-facing surface, which may be symmetrical in the longitudinal aspect and which provides a concave surface upon which the fingers can gain purchase. The disc grip portion 213 includes at least two distally-extending lateral projections 212, opposite each other on the disc, which can be used to help manipulate the control handle. Such a concave disc 211 therefore effective provides any number of possible finger placements, as may be preferred, as if the proximal inner surface of the finger loops were extended through 360 degrees around the main longitudinal axis of the control handle. Additionally, surface features can be provided on the underside of the round disc grip portion such as to improve the grip on the device. The two-finger grip portion 113 of FIGS. 8a-8b also includes distally-extending lateral projections 112 similar to those of the disc-shaped grip portion, and which also aid in the control and manipulation of the grip portion and thus the control handle having such a grip portion.

The LVF reservoir 22 is adapted for containing an incompressible fluid, which is preferably sterile, non-toxic and having a low viscosity, such as distilled water and/or a saline solution for example. Although other capacities are possible, in one embodiment the LVF reservoir is capable of containing a volume of approximate 20 cubic centimeters (cc) of fluid. The substantially cylindrical LVF reservoir 22 is defined by a tubular wall 23 which is preferably composed of a clear or translucent material, such that the surgeon is capable of seeing through the outer wall of the LVF reservoir 22 in order to be able to visually determine the quantity of liquid therewithin. In this respect, graduation markers may be provided on the clear tubular wall of the LVF reservoir 22 such as to permit, upon visual inspection, the identification of a level of liquid within the LVF reservoir 22, both before and after injection of a volume of the low viscosity liquid from the LVF reservoir 22 into the bone cement reservoir 14, as will be described further below.

In order to better permit this visual indication, a substantially doughnut shaped second plunger 24 is disposed within the LVF reservoir 22 and is longitudinally displaceable (i.e. sliding) within the tubular wall 23 in direct response to the amount of LVF contained in the LVF reservoir 22. The second plunger 24 forms a seal with the tubular wall 23 (either by itself and/or with the additional assistance of an o-ring seal 25 therebetween), which still permitting sliding displacement relative thereto, such as to keep the LVF reservoir 22 substantially air free during the injection procedure. Thus, the second plunger 24 acts as a displacing end wall which moves longitudinally towards the outlet end (i.e. proximal) of the control handle 12 as the amount of LVF within the reservoir reduces (i.e. following injection of LVF into the cement reservoir 14). The second plunger 24 is so displaced regardless of the orientation of the control handle. The second plunger 24 thus additionally serves as a liquid level guide by forming a visual marker relative to the graduation markings on the wall 23 of the LVF reservoir 22 and/or a slider as described below, which allows for given positions of the plunger to be marked. The sliding may be provided either internally or externally to the reservoir 22, and may for example be used to mark the starting position of the plunger before it is displaced. The slider therefore provides a reference point which, together with the relative position of the displaced plunger, can be used by the surgeon to visually determine the volume of LVF expelled from the LVF reservoir 22 and thus the volume of bone cement ultimately injected into the bone site. Accordingly, displacement of the second plunger 24 within the LVF reservoir 22 permits the surgeon to accurately determine the quantity of low viscosity liquid which is injected out of the control handle 12, which corresponds closely to a quantity of bone cement which is forced out of the bone cement reservoir 14, though the cannula 18 and into the vertebral body. In another embodiment, the graduation markers may be provided on a sliding component (e.g., a clear, C-shaped section of tube, or a full tube) that snaps onto or is otherwise disposed upon and closely mating with the outer surface of the LVF reservoir 22 such that the graduation markers may be set or reset to zero at any time by sliding this component relative to the LVF reservoir and thus relative to the longitudinally displaceable plunger. Such sliding graduation markers would be especially useful in between levels of a multi-level procedure, in order to track the volume of cement injected from zero each time.

The grip portion 13 of the control handle 12 provides the surgeon with sufficient gripping surface area in order to apply a required force but also permit the surgeon to impose an orientation to the device, for example permit the control handle to be easily rotated, inclined, inverted, etc. as may be desired. The configuration of the inlet check valve 40 within the LVF reservoir 22 precludes the entry of air bubbles, should any exist in the LVF within the reservoir, such that regardless of the orientation given to the control handle there is no risk of any air bubbles entering into the power piston tube 28. This is due to the fact that the inlet check valve 40 is located near the outlet end of the control handle, which can never be near the surface of the LVF fluid within the reservoir where any air would rise to.

As seen in FIG. 2, the power piston assembly 20 of the control handle 12 includes the first plunger 26 which is depressed by the user's thumb and which slides longitudinally within an inner power piston tube 28 extending down through the center of the LVF reservoir 22 and fixed in position therewithin. The first plunger 26 is outwardly biased by a helical spring 30 which, in one embodiment may surround the first plunger 26 between the plunger head 32 at one end and the outer end 34 of the power piston tube 28 at the other.

Figure 11:
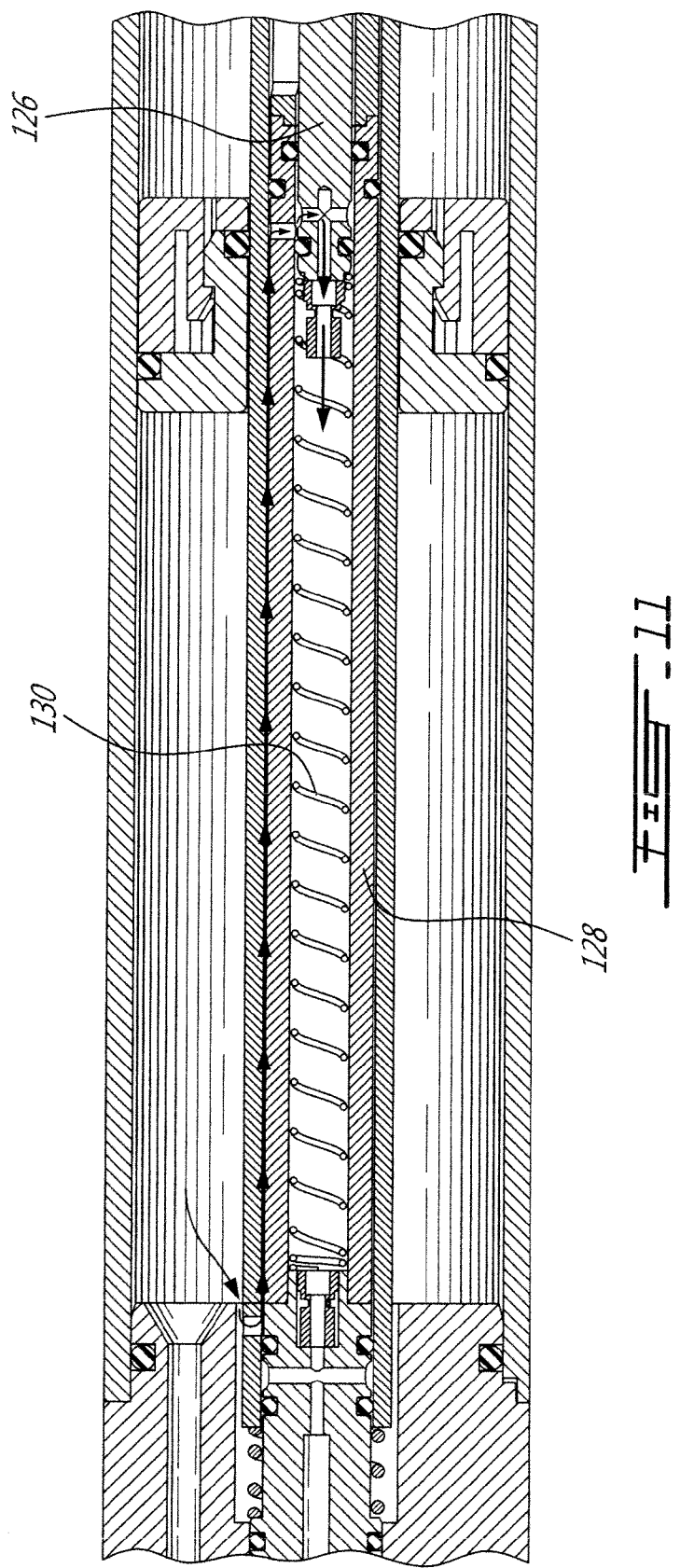
FIG. 11 is a partial, cross-sectional view of an alternate control handle of the present system, having the power piston plunger spring internally mounted therewithin.

Alternately, however, the helical spring 30 may be located fully within the power piston assembly, instead of being external thereto as shown in FIG. 2-3. In this alternately embodiment, the spring functions in the same matter, however is retained within the body of the power piston, such as within a thin-walled protective tube which acts as a concealing sheath and has two concentric tubular walls between which the spring is received. This thin-walled double tube may be an additional component which fits concentrically about the power piston tube 28. This internal mounting of the spring permits the power piston assembly to be externally smooth, without any external pinch-points of the spring being possible as it compresses along its length. In another similar embodiment, as depicted in FIG. 11, the spring 130 is disposed entirely within the inner power piston tube 128 itself, obviating the need for any additional protective tube. The spring 130 in this embodiment simply remains within the internal passage of the piston tube 128 through which the LVF is expelled by the first plunger 126 as it is depressed.

In both of the above two described embodiments the spring is internal rather than external, further simplifying the overall look of the device. This may also have the added advantage of simplifying sterilization of the device. In at least one embodiment, the spring 30 is comprised of two separate spring parts linked together by a spring connector 36 which is disposed between the two and which additionally helps to locate the spring in position about the body of the first plunger 26.

Although other volumes (ranging from 0.25 cc to 2 cc) are possible, in a typical embodiment the power piston has a 0.5 cc capacity, in that a 0.5 cc volume of the LVF liquid is capable of being drawn into the power piston tube 28 for injection out of the control handle 12, with each depression of the first plunger 26 of the power piston 20. The surgeon actuates the device by depressing the spring loaded first plunger 26 of the power piston 20, which generates sufficient fluid force due to the relatively small cross section of the plunger and the mating power piston tube 28. The LVF is thereby forced out of the power piston tube 28, through a check valve assembly 35, and out of the control handle 12 via an outlet port 38. In order to fill a typically sized lumbar vertebra, 12 to 16 full length depressions of the first plunger 26 may be needed in order to eject a total of 6-8 cc of LVF out of the power piston.

Only one-way advancement of the low viscosity fluid, from the power piston assembly 20 of the control handle 12, through extension tube 16 and into the cement reservoir 14, is permitted during normal operation. This is achieved in one embodiment by using a check valve assembly 35 disposed between the outlet port 38 of the control handle 12 and the outer end 29 of the power piston tube 28. In this embodiment the check valve assembly 35 includes at least two check valves. The first one-way check valve 40 is an inlet check valve which allows the low viscosity fluid within the reservoir 22 to be drawn into the power piston tube 28 via an inlet port 41, for example when a vacuum is generated therein when the first plunger 26 of the power piston 20 is displaced outwardly away from the check valve assembly 35 by the force of the spring 30. The second one-way check valve 42 allows the LVF only to be injected out of the power piston 20, such as to prevent the LVF fluid returning back into the control handle, and thus permits the displacement of LVF into the cement reservoir 14 once forced out of the control handle. Accordingly, because of the one way flow imposed by the two check valves, the system can be operated by depressing the first plunger 26 of the power piston 20, thereby forcing the LVF out of the control handle 12 via the check valve assembly 35, through the extension tube 16 and into the cement reservoir 14, thereby displacing a same amount of the high viscosity fluid out of the cement reservoir.

Figure 7A:
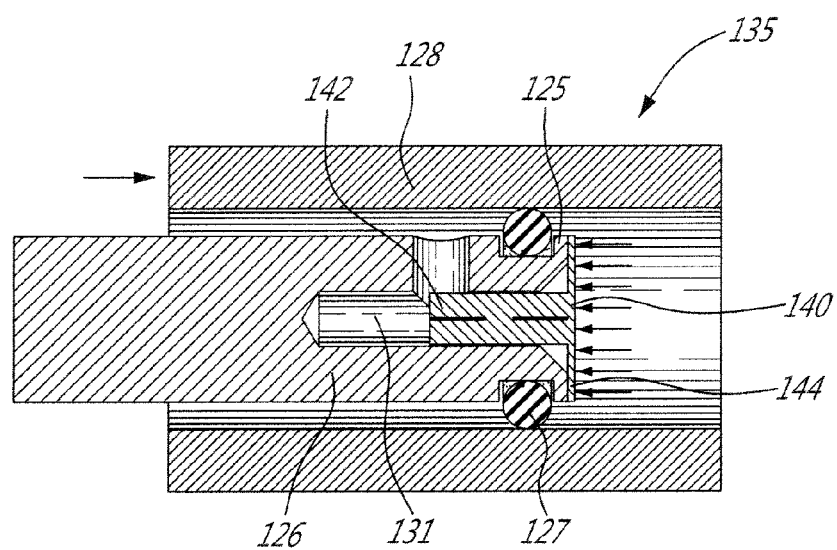
FIG. 7a is a partial cross-sectional view of a power piston plunger of an alternate control handle, the plunger having an integrated check valve shown in the closed position.
Figure 7B:
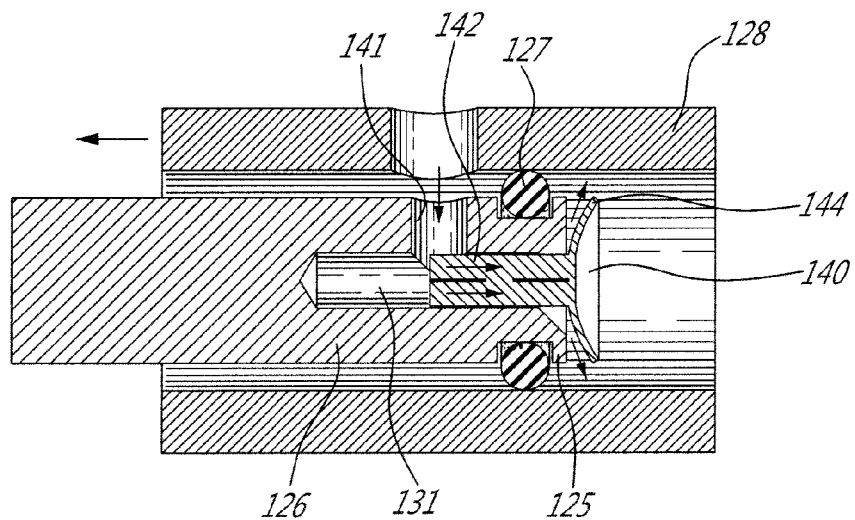
FIG. 7b is a partial cross-sectional view of a power piston plunger of an alternate control handle, the plunger having an integrated check valve shown in a open position.
Figure 7C:
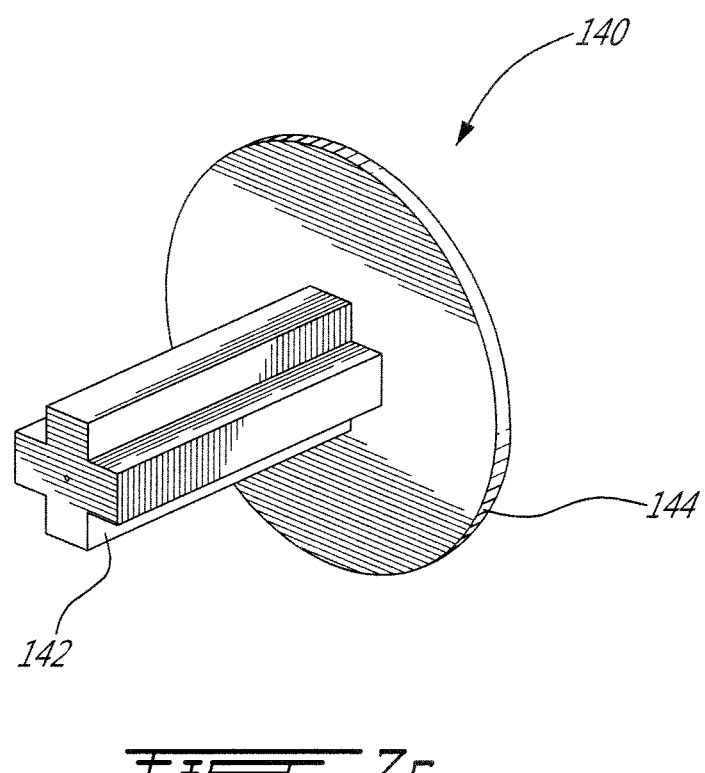
FIG. 7c is a perspective view of a check valve plug of the plunger check valve of FIGS. 7a and 7b.

In an alternate embodiment, as shown in FIGS. 7a-7c, the one way advancement of the low viscosity fluid out of the control handle, when the power piston is actuated by depressing the first plunger 126 thereof, is achieved using a check valve assembly 135 which employs a check valve plug 140 that is integrated directly into the tip 125 of the first plunger 126 of the power piston, in lieu of the check valve assembly 35 described above. The check valve plug 140 is such that it closes when the plunger 126 is depressed (moving to the right in FIG. 7a), thereby forcing the LVF out of the power piston and thus the control handle, but opens when the plunger is moved in the opposite direction (moving to the left in FIG. 7b). Therefore, in this embodiment, the tip of the plunger 126 has a longitudinal through-hole that bypasses the front sealing o-ring 127 of the plunger when the check valve plug 140 is open, and which vents behind the o-ring through a side port 141 that is in continuous fluid communication through one or more passages with the surrounding LVF reservoir.

When the piston 126 is moved outwardly as shown in FIG. 7b, a suction is created which draws the LVF in from behind the o-ring seal 127 via the inlet port 141 in the side of the plunger tip 125, through the central body 142 of the check valve plunger 140 and out of the plunger tip 125 via an annular outlet port 129 therein and thus onto a pressure side of the plunger 126, thereby completely filling the tube in preparation for the subsequent stroke (plunger depression). This flow of the LVF is represented by the arrows in FIG. 7b. The LVF is able to flow through the central body 142 of the check valve plug 140 due to the cross-sectional geometry thereof, which one or more passages extending fully through the length of the central body. In one particularly embodiment, as shown in FIG. 7c, the central body 142 of the check valve plug 140 has a cruciform shaped cross-sectional profile, which therefore allows for four parallel "channels" for the LVF flow through the check valve created by the check valve plug 140 when mounted into the open end of the plunger tip 125. The central body 142 of the check valve plug 140 may be press fit into the cylindrical passage 131 centrally defined in the plunger tip 125, or by other suitable fastening, locking and/or engagement means.

The check valve plug 140 is preferably made from a flexible elastomeric material, such as silicone or thermoplastic vulcanizate (e.g. Santoprene®) for example, and includes an at least partially flexible disc portion 144 at the end of the plunger 126 which is displaced away from sealing engagement with the plunger tip 125 when the plunger 126 is drawn outward as described above and shown in FIG. 7b. Once the piston 126 is fully drawn outwardly, subsequently depressing the plunger 126 will cause the pressure generated by the water on the pressure side of the sealed plunger tip (i.e. right side of the plunger in FIG. 7a) to seal the outer disc portion 144 of the check valve plug 140 against the plunger tip 125, thereby closing the check valve assembly 135. As the plunger is depressed the LVF fluid on the pressure side of the sealed plunger tip is therefore forced out of the power piston tube 128.

Alternately still, the check valve assembly can include a steel ball check valve similar to the first check valve 40 of the check valve assembly 35, and which serves a similar function, namely to allow the low viscosity fluid within the reservoir 22 to be drawn into the power piston tube 28 when open while forcing the low viscosity fluid out of the power piston tube when the plunger is depressed. Such a steel ball check valve may either be disposed in a check valve body as per the check valve assembly 35 or may be incorporated directly into the tip of the plunger of the power piston as per the check valve assembly 135.

Referring back to the embodiment of FIG. 2, another check valve 44 may also be provided and acts as a safety relief valve. This check valve 44 is actuated by an overpressure release mechanism 45, including an actuating button 46 which is interconnected with one end of a displaceable connecting pin link 48, the other end of which is engaged with the check valve 44. The button 46 is disposed at the outer end of the control handle proximate to the finger grip portion 13 and the plunger 26 of the power piston 20, such as to permit ease of access by the surgeon, typically by the thumb. The pressure relief actuating button 46 may be provided on a single side of the finger grip portion as shown in FIG. 1, however preferably this pressure relief actuating button 46 is in fact annular and concentric with the plunger 32 of the power piston and thus with the central axis of entire the control handle (as shown in FIG. 2). Such a concentric, annular button 46 permits the user of the device to easily access and depress the pressure relief button 46 at any point thereon and therefore from any orientation, regardless of the grip selected by the user. This improves the ability of the user to easily and safely actuate the button 46, in an emergency situation for example, at any point and from any orientation. This helps to improve the overall safety and ease of operation of the control handle and the entire system. When the concentric annular button 46 is depressed, the connecting pin link 48 is translated, thereby actuating the check valve 44 such as to permit the LVF beyond the second check valve 42 to return to the LVF reservoir 22 by bypassing this second check valve 42, and thereby preventing further displacement of the LVF fluid within the extension tube 16 (and thus into the LVF cavity portion of the cement reservoir 14). The safety or overpressure relief check valve 44 allows almost instantaneous removal of the force acting on the LVF by the power piston, thereby immediately stopping further displacement of the LVF through the system.

The control handle 12 of the present system, including all of its control elements (e.g., power piston, overpressure relief check valve), is particularly useful in that it can be operated at a distance, as the control handle 12 is remote from the cement reservoir 14 due to the extension tube 16, and thereby avoids or limits the surgeon's exposure to the radiation, caused in the surgical field for example by the fluoroscopic imaging used for guidance during the procedure.

Referring now to FIGS. 10a-10d, a control handle 112 having a safety or overpressure relief mechanism 145 is shown, which may be used in place of the third check valve 44 described above. The safety relief mechanism 145 obviates the need for the eccentric pin 48 used to activate the third check valve 44 as described above, and, indeed, the third check valve 44 itself. The safety relief mechanism 145 depicted in FIGS. 10a-10d uses a system of ports and o-rings, instead of the directly acting pin link 48, to accomplish a similar function. The advantages with the port and o-ring system of the safety relief mechanism 145 are principally that the control handle is truly concentric, and therefore easier and more cost effective to manufacture and assemble, as well as more compact and reliable. The safety relief mechanism 145 uses the same actuating button 46 as in the previously described embodiment, but the button 46 is connected to a safety pressure relief tube 148 which is concentric with the power piston 20. The pressure relief tube 148 is thus translated within the control handle when the button 46 is depressed. The pressure relief tube 148 includes a small opening 149 located in the sidewall of the tube at the distal end thereof. This opening 149 will allow for fluid flow between the low viscosity fluid (LVF) reservoir 22 and the power piston 20, as will be described.

Figure 10A:
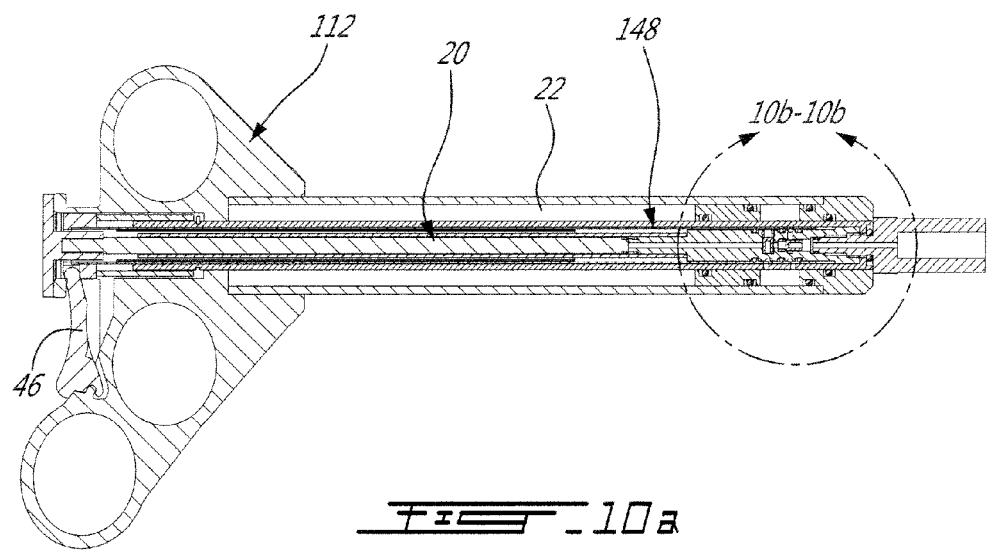
FIGS. 10a to 10d show cross-sectional side views of an alternate control handle having an alternate safety relief mechanism therein.
Figure 10B:
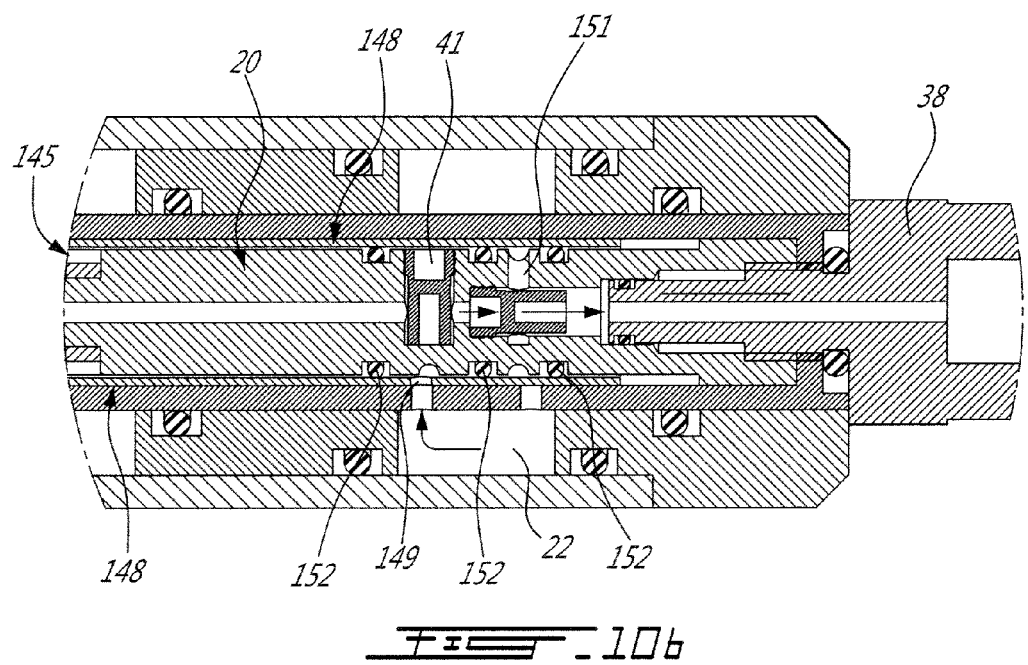
Figure 10C:
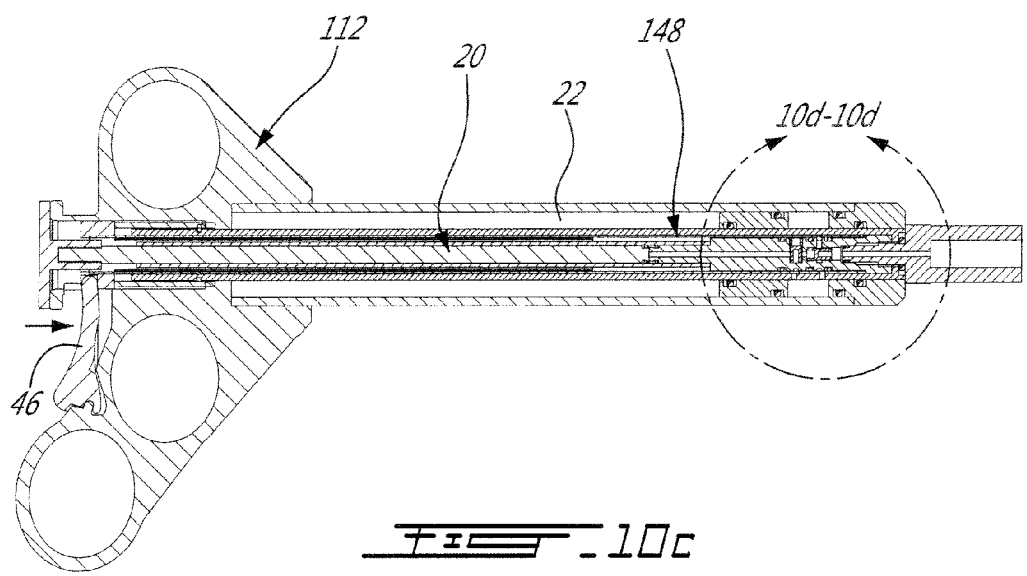

In normal operation, the pressure relief button 46 is not depressed (as shown in FIG. 10a) and the position of the opening 149 in the safety relief tube 148 is positioned so that the flow of low viscosity fluid can enter the inlet port 41 and pass through to the outlet port 38 of the control handle 112. At this time, the pressure relief port 151 is covered and thus sealed from any fluid exchange. The arrows shown in FIG. 10b show the flow of the low viscosity fluid during normal operation. When there is a need to immediately stop the flow of cement, the safety relief button 46 is depressed and as a result the safety relief tube 148 is advanced within the control handle (as shown in FIG. 10e), such that the opening 149 at the distal end of the tube 148 is lined up with the safety relief port 151 to allow for the communication of the LVF back into the LVF reservoir 20, as shown in 10d. At the same time, the safety relief tube 148 covers the inlet port 41. The flow of LVF back into the LVF reservoir is shown by the arrows in FIG. 10d.

Figure 10D:
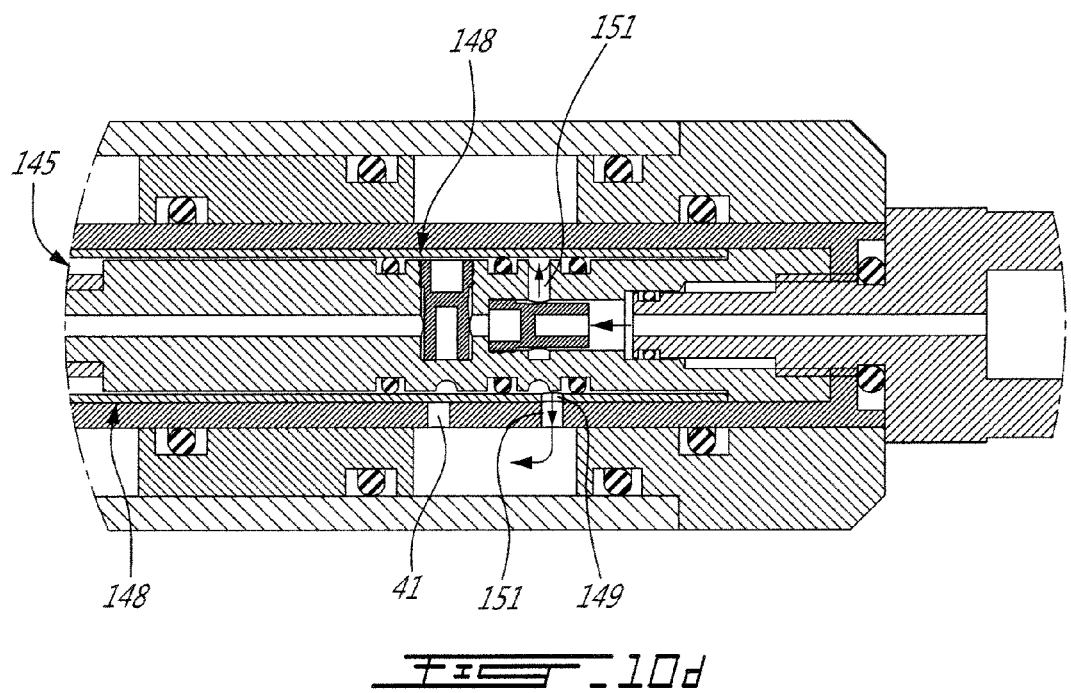

In addition to the possible manual actuation of the safety relief system, the port and o-ring system can also provide an automatic overpressure relief mechanism that can be designed to operate at any desired pressure. Referring to FIG. 10d, and specifically to the three o-rings 152 of the safety relief system, wherein the middle of which o-rings acts as a separator between the inlet port 41 and the safety relief port 151. The effective sealing pressure of this middle o-ring can be selected and adjusted through a very wide range by controlling the o-ring durometer and its percent compression, the width and depth of the o-ring groove in the central barrel, and the clearance between the inside diameter of the sliding safety relief tube 48 and the outside diameter or the central barrel housing constraining the o-rings. For example, by using an o-ring having a low hardness (i.e. a low durometer value) with very little compression (such as between 1-5% for example) and a large clearance, the LVF on the high-pressure side of this middle o-ring 152 will "blow by" the middle o-ring (that is the o-ring will not be able to prevent the LVF from flowing partially past it) at a low pressure (as low as 0.1 MPa, for example) and thus result in a fluid transfer back into the LVF reservoir. Whereas using an o-ring of high durometer, with a high percentage of compression (15-20% or possibly more), and very little clearance between the safety relief tube and the central barrel housing, would result in an o-ring capable of withstanding extremely high pressures (10-20 MPa or more). Therefore, the o-ring seal may be designed and provided such that it allows leakage at a given predetermined threshold pressure which is selected such as to act as in integral overpressure relief which is otherwise not reliant on moving parts, etc. By thereby controlling the "blow-by" pressure of the middle of the three o-rings 152, the system has a built-in, automatic, reversible overpressure safety relief that can be designed to seal at pressures required for cement injection, but to relieve pressure before mechanical integrity of the devices such as the LVF extension tube and the cement reservoir is compromised.

Referring now back to FIG. 2, the overall design of the control handle 12 is such that it is more ergonomic than known injection devices, for example by having the LVF reservoir 22 concentric with the central power piston 20. The control handle can be operated one-handed, equally well with the left or the right hand (symmetrical design). A surgeon can operate two independent injections concurrently (e.g., for multi-segmental procedures), holding one control handle each in the left and right hand. Further, as noted above, the displacing plunger 24 which is disposed within the LVF reservoir 22 and is constrained to slide over the power piston tube 28, acts both as a visual indicator of the amount of LVF and thus the bone cement injected and also serves as a sliding seal which retains the fluid within the LVF reservoir 22. As such, o-ring or other types of sealing elements are provided on both the outer diameter and the inner diameter of the annular plunger 24, such as to respectively form a seal with the inner surface of the reservoir wall 23 and the outer surface of the power piston tube 28.

Turning now to the extension tube 16 and the embodiment of the bone cement reservoir 14 as seen in FIG. 2 in more detail, the extension tube has a first end 17 which is connected to the outlet port 38 of the control handle 12 at an opposite second end 19 which is connected to the bone cement reservoir 14. Preferably, quick-connect type swivel couplings 21 are used to easily and removably engage the first and second ends 17, 19 of the extension tube 16 to the control handle 12 and the bone cement reservoir 14, respectively. The swivel connectors 21 help by permitting the control handle to move freely without inadvertent torque and moment loading on the cannula, which may otherwise lead to stress and possibly a fracture of the osteoporotic pedicle, or kink the extension tube. In an alternative embodiment, the extension tube may be permanently mounted to the injector (control handle) and the cement reservoir. For example, as the cement reservoir can rotate within the cannula, inadvertent torque forces are equally avoided. The swivel connector 21 on the second end 19 of the extension tube 16 is releasably engaged with a quick release coupling 15 mounted to the upper end of the egg-shaped bone cement reservoir 14. Each reservoir 14 is therefore said to be an "egg", which may be pre-filled with bone cement and mounted to a cannula. The extension tube 16 is preferably made of an extremely stiff and substantially non-compliant, yet flexible, material such as to prevent the build-up of significant stored strain energy therein. Otherwise, energy stored in the extension tube could potentially cause the bone cement to be forced out of the cement reservoir 14 in an uncontrolled manner during the procedure. The extension tube 16 may be selected such as to have any desirable length (typically 50 cm, ranging from 30 cm to 80 cm, but potentially can have any length), as may be necessary to interconnect the control handle 12 and the bone cement reservoir 14.

The reservoir 14 has a body shape (or geometry) which is preferably substantially spherical, such as to permit for a maximum hydraulic stiffness and therefore minimum compliance of the reservoir body. However, it is to be understood that the reservoir 14 may have a body shape which is not exactly and/or entire spherical, for example it may alternately be oblong or oval.

As noted above, the control handle 12 is used to displace the LVF out of the exit port 38 of the handle 12, through extension tube 16, and into the bone cement reservoir 14.

Figure 4:
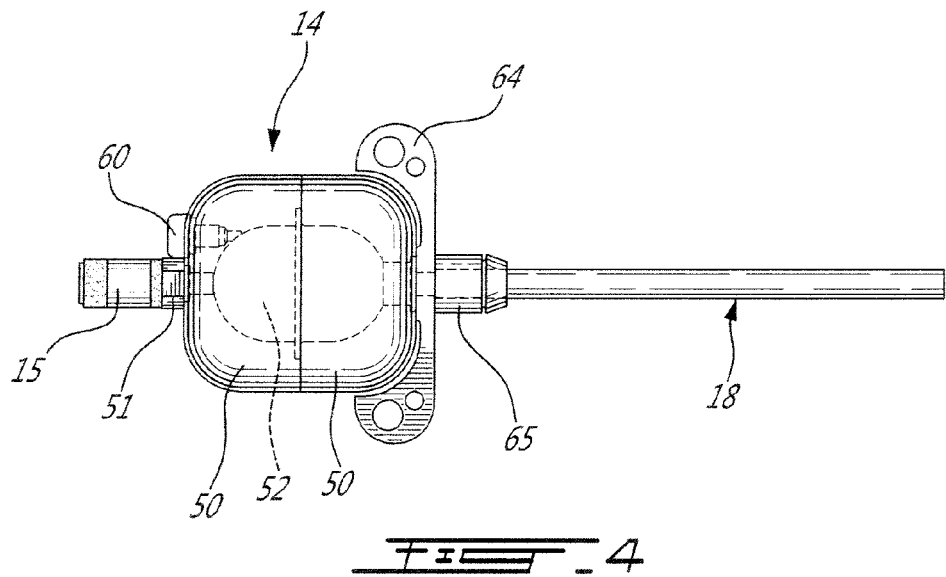
FIG. 4 is a side view of the cement reservoir of the cement injection system of FIG. 1, mounted to the cannula.

Referring to FIGS. 2 and 4, the bone cement reservoir 14 comprises two halves 50, each of which is composed of a generally cylindrical body having an open topped concave cavity formed therein such that when the two cylinders are fastened together with the two cavities facing each other, the reservoir so formed has an enclosed cavity 52 therein. In one embodiment, the cavity 52 defines an oblong shape, in other words one which comprises a cylindrical middle section and opposed hemispherical concave ends. As such, the cavity defines a shape that is symmetrical about a central plane extending transversely through the cavity 52 and the surrounding body of the reservoir. The concave ends of the cavity 52 were chosen to be hemispherical as a result of cement extrusion experiments, which showed that the optimized shape of the bone cement as it was forced through the cavity by a diaphragm was a hemispherical one. This hemispherical shape ensures a volumetrically maximized and stiffest possible design for the cement reservoir 14 and thus minimizes the stored energy in the system due to strain. A number of suitable materials may be used for the two cylinder halves 50, however in one embodiment they are made of polycarbonate cylinders which are removably fastened together. In one possible embodiment, the two halves 50 of the cement reservoir 14 are bolted together, however other fastening means can be used, whether by a permanent fastening method such as gluing or an alternate removable fastening method such as a screw connection, snapping fasteners, etc. The fastening method must however be able to withstand considerable forces (for example, up to 5,000 N) pushing the two cylinder halves apart, due to the large forces inside the bone cement reservoir. Advantageously, the cavity 52 of the bone cement reservoir 14 is sufficiently large, i.e. contains a sufficient volume of high viscosity bone cement, to be able to provide the complete injection of the necessary amount of bone cement into the vertebra in only one application, i.e. without needing to be refilled. For example, in the case of injecting bone cement in a single vertebra of lumbar region, the cavity 52 can supply at least the estimated 8-10 cc of bone cement used maximally in a single vertebral body injection.

Figure 5:
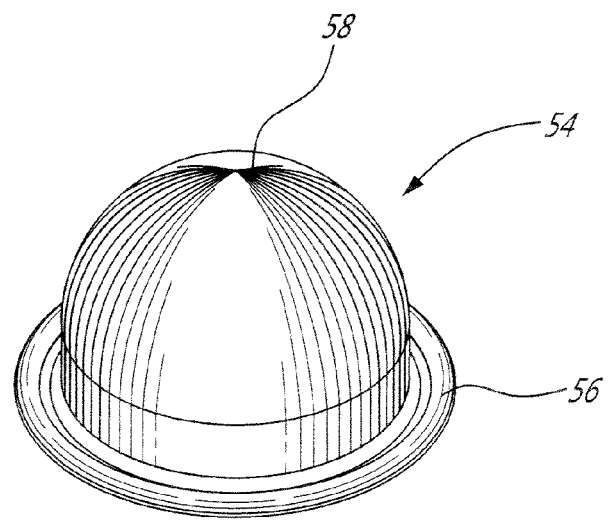
FIG. 5 is a perspective view of a diaphragm of the cement reservoir of FIG. 4.

The cavity 52 within the cement reservoir 14 is separated by a diaphragm 54 which fits therewithin and, as seen in FIGS. 2 and 5, comprises a generally hemispherical size and shape corresponding to the inner contours of each half of the cavity 52. As the diaphragm 54 fits precisely within and abuts directly against the inner surfaces of the opposed end walls of the cavity 52, the amount of air introduced into the system when primed with the low viscosity fluid is minimized. The diaphragm 54 preferably includes an integrated o-ring 56 about the outer periphery thereof, which is intended to help anchor the diaphragm between the two halves 50 of the cement reservoir 14, and also serves to seal the two halves up to very high pressures, such as up to 1500 psi for example. The tip portion 58 of the diaphragm 54 may have an increased thickness, i.e. the thickness of the tip portion 58 may be greater than the thickness of the remainder of the diaphragm wall. This is done so that the diaphragm will not tear once it reaches either end of the cavity 52 of the cement reservoir 14. Further, this increased thickness at the tip 58 prevents further distension and/or damage of the diaphragm 54, through extrusion, into the cannula, should this ever occur. Further, this increased thickness of the tip or nose of the diaphragm also helps to provide additional tactile feedback to the surgeon to indicate that no more cement can be injected. For example, a sudden increase in resistance may be felt at the power piston 20 of the control handle 12 when the diaphragm 54 reaches its fully displaced position within the bone cement reservoir 14 and the thick diaphragm tip abuts the solid inner surfaces of the cavity 52. Although in many, and practically all, cases the injection of the high viscosity material will be stopped by the surgeon well before the diaphragm reaches this point (i.e. fully abutted against the inner surface of the reservoir cavity), as a majority of bone elements will require the injection of less cement than the capacity of the high viscosity cement within the reservoir 14.

The diaphragm 54 therefore acts as a material-moving membrane which distinctly separates the incompressible LVF and the more viscous bone cement on either side thereof within the bone cement reservoir. While the diaphragm is displaceable by the pressurized LVF, no other moving mechanical parts are present in the bone cement reservoir 14 for the displacement of the high viscosity bone cement out of the cavity 52 in the reservoir 14 and through the cannula 18 to the vertebral body. The diaphragm is preferably very pliable to maximize the tactile feedback to the surgeon and thus improve the surgeon's ability to accurately control cement flow. The diaphragm may be thin walled but having adequate strength and may be made of polyurethane, silicone, polyolefin, thermoplastic vulcanizate or any other non-toxic, bio-compatible material. The diaphragm may be largely non-compliant, in that it is composed of a material that, upon being completely filled, demonstrates a relatively sharp pressure rise while assuming a specific predefined shape and dimension. The diaphragm however preferably remains flexible, in that it is relatively supple, displaceable and/or deformable. Such a largely non-compliant diaphragm, as opposed to a more pliant diaphragm, may have a more controlled action of folding over from the proximal to the distal fully distended shape, and may be stronger.

The diaphragm is made of a flexible material, such as silicone for example, so that it is capable of being inverted and thus displaced from one side of the cavity 52 to the opposed other side thereof. For example when the cavity 52 is charged with bone cement to be injected into the bone element, the diaphragm is disposed in the initial position shown in FIG. 2, whereby it is located on an outer side (i.e. away from the cannula 18) of the inner wall of the cavity 52. Once the LVF is forced into the cement reservoir 14 via the inlet 51, the diaphragm is forced by the pressurized LVF to displace inward towards the cannula side of the cavity 52, thereby displacing the high viscosity bone cement contained within the cavity 52, on the other side of the diaphragm 54, out of the cavity 52 of the bone cement reservoir 14 and through the cannula 18 to which the bone cement reservoir 14 is mounted. The diaphragm 54 thereby acts as a material moving membrane which, due to the pressurized LVF acting on the other side of the diaphragm, forces the bone cement out of the cavity 52 and therefore out of the bone cement reservoir 14 via the outlet port 55. Accordingly, the diaphragm corresponds to the shape of the cavity 52 of the bone cement reservoir 14 and is displaced therein by the LVF fluid acting thereagainst, and as such there are no frictional effects to contend with and the surgeon will therefore have a better perception (i.e. tactile feedback) of the injection force.

Figure 12:
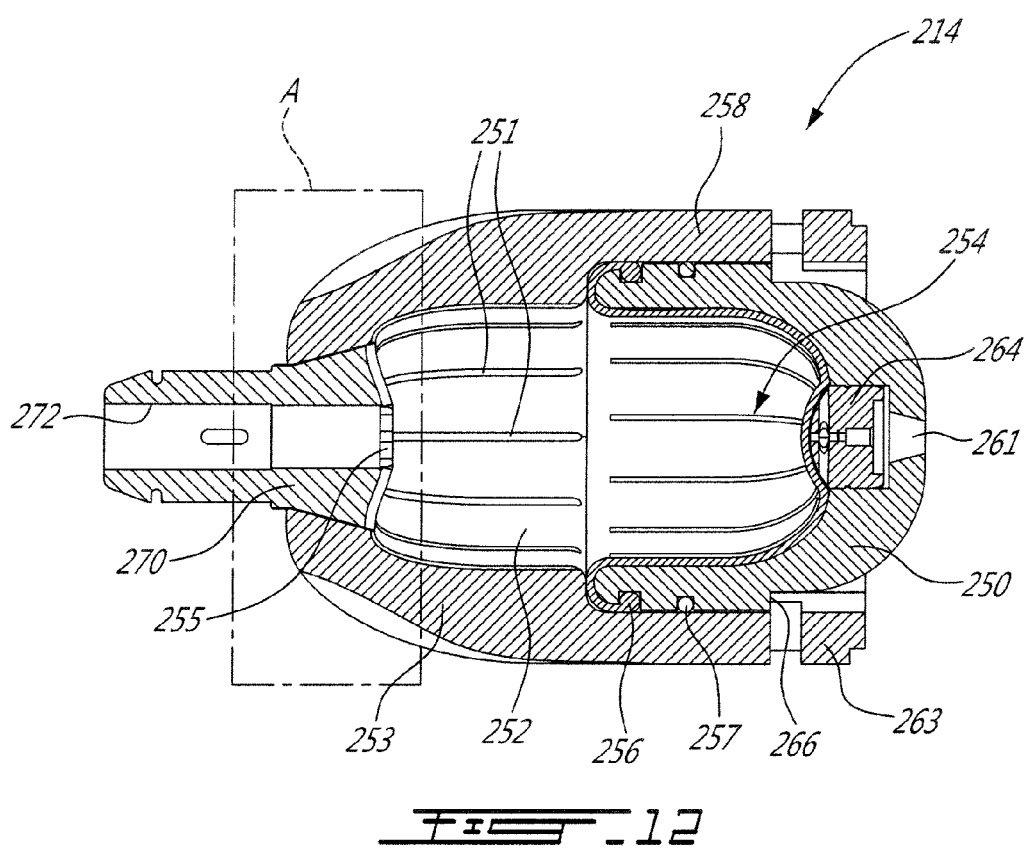
FIG. 12 is a cross-sectional view of a bone cement reservoir in accordance with an with an alternate embodiment.
Figure 13:
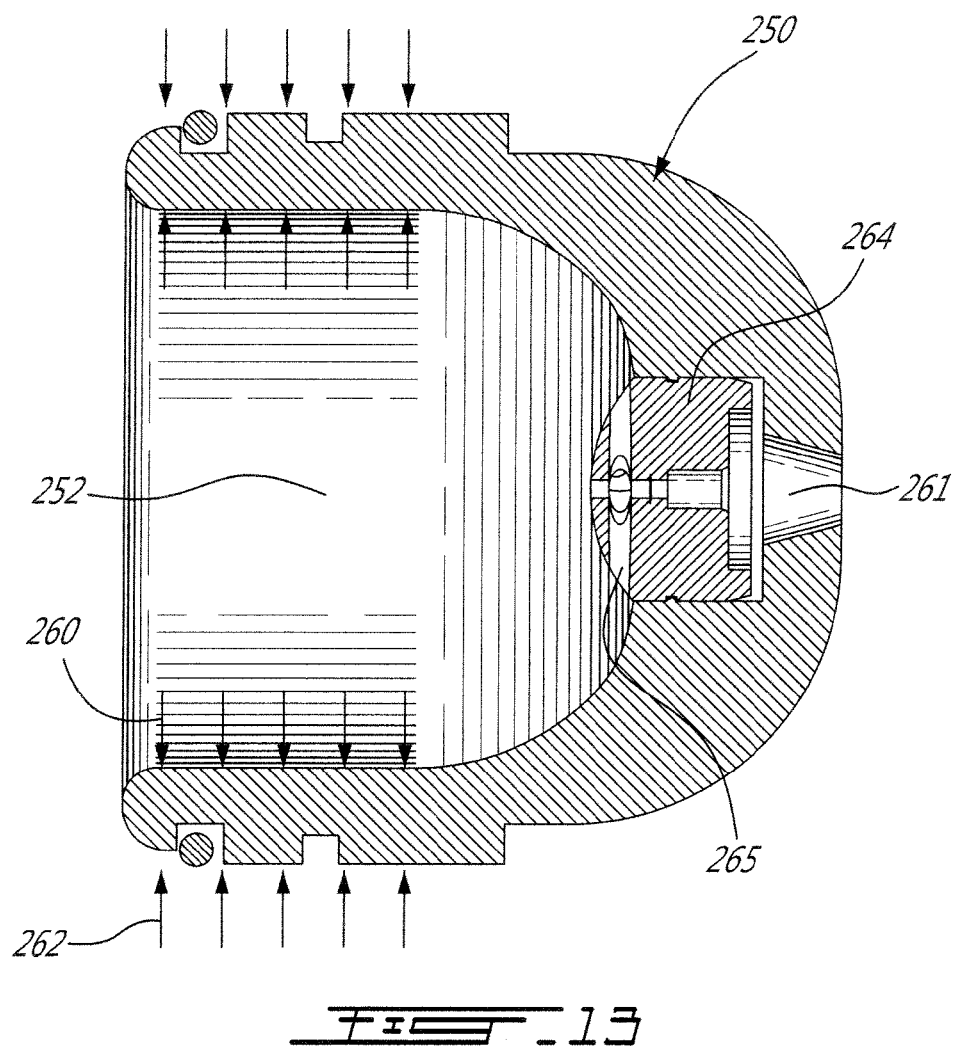
FIG. 13 is a cross-sectional view of a proximal half portion of the bone cement reservoir of FIG. 12.

Referring now to FIGS. 12 to 16, a bone cement reservoir 214 in accordance with an another embodiment is shown which operates in much the same way as the reservoir 14 describe above, however includes several additional features. As seen in FIGS. 12-13, the bone cement reservoir 214 is comprised of two mating portions which interlock together, namely a proximal half 250 and a corresponding distal half 253. As can be seen, the proximal half 250 actually fits within and mates with a corresponding opening in the distal half 253 and therefore forms a laterally sealed engagement therewith the help, for example, of a ring seal 257 and the annular outer rim 256 of the diaphragm 254, which is received between the two mating halves such that the diaphragm body fits within the internal cavity 252 formed within the reservoir 214 when the two half portions are sealing engaged together as shown in FIG. 12. Once so mated, a nut 263 which is proximally located and surrounds the proximal half 250 abuts against an annular flange 266 on the proximal half 250 and is threadably engaged with the distal half 250 of the reservoir body, such that when tightened the nut 263 fastened the two halves 250, 253 of the reservoir body together in sealing engagement.

Because the proximal half 250 of the reservoir body fits within, and is surrounded by the annular wall portion 258 of the distal half 253, increasing the internal pressure within the cavity 252 formed when the two halves are engaged together as shown in FIG. 12 will cause the proximal half 250 to be forced radially outward into even greater sealing contact with the annular wall portion 258 of the distal half 253 of the reservoir body. As seen in FIG. 13, as the internal pressure within the cavity 252 increases (as represented by the outwardly facing arrows 260), the radial seal (as represented by the inwardly facing arrows 262) between the two halves 250, 253 of the reservoir body will become even more effective. This design permits the bone cement reservoir 214 to handle high pressures without risk of a seal breakdown or leakage of either bone cement or LVF.

Figure 14:
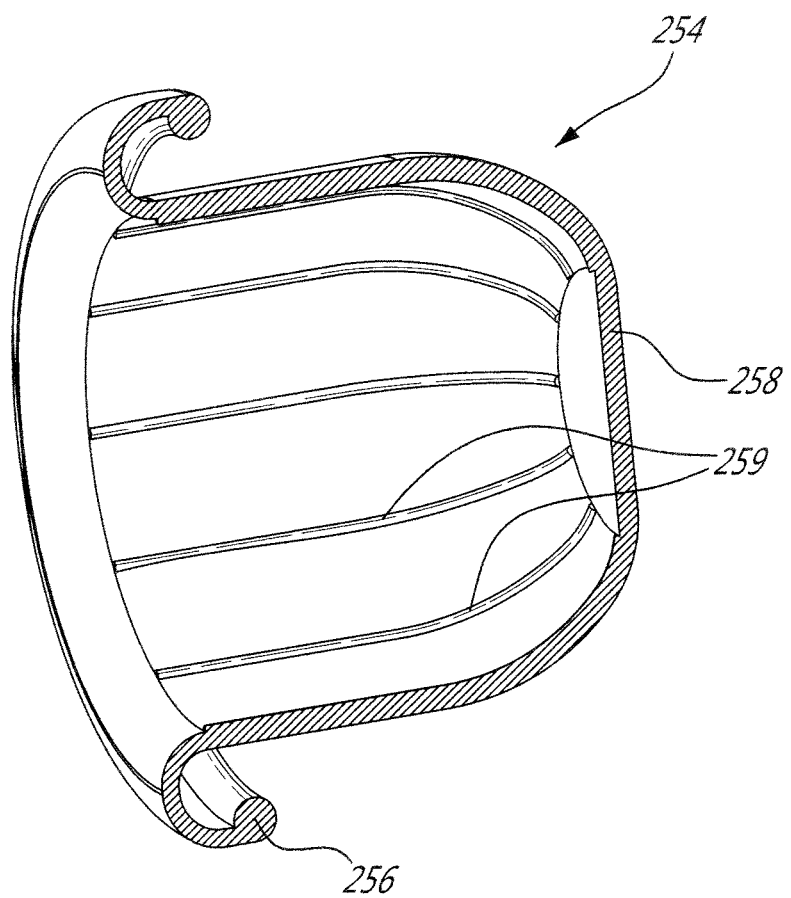
FIG. 14 is a partially sectioned perspective view of a diaphragm of the bone cement reservoir of FIG. 12.

The diaphragm 254 used within the bone cement reservoir 214 functions and generally corresponds in material, shape, etc. as per the diaphragm 54 described above with respect to the earlier described embodiment, and acts to separate the LVF from the bone cement within the internal cavity 252 of the bone cement reservoir 214 such that the bone cement and the LVF do not come into contact with each other, yet such that the LVF is able to apply sufficient pressure on the diaphragm to force the ejection of the bone cement on the opposite side of the diaphragm out of the reservoir 214 via outlet port opening 255 for injection into the desired bone element. As seen in FIG. 14, the diaphragm 254 includes a plurality of ribs 259 on an inner side thereof which extend between the central tip 258 and an outer annular edge proximate the surrounding annular peripheral rim 256. The ribs 259 on the cement-contacting surface of the diaphragm 254 help the diaphragm to unfold (or rather inverse itself) in such a manner which substantially maximizes the removal of cement therefrom. The diaphragm 254 is shown in FIGS. 12 and 14 in its 'relaxed' or starting state, that is when the entire cavity of the bone cement reservoir is filled with bone cement (i.e. prior to injection of the bone cement). As can be seen in FIG. 12, the inner surface on the distal half 253 of the bone cement reservoir which partially encloses the cavity 252 includes a plurality of grooves 251 therein which correspond to and are adapted to receive the raised ribs 259 on the diaphragm 254, when the diaphragm is fully displaced into a distended position following the complete ejection of bone cement out of the cavity 252.

As seen in FIGS. 12 and 13, the proximal half 250 of the reservoir 214 body includes a de-airing plug 264 on the LVF side of the diaphragm, within the LVF inlet port 261 to the reservoir 250 and its internal cavity 252. The de-airing plug 264 permits LVF to flow centrally through it in the LVF injection direction (i.e. to the left in FIGS. 12 and 13), however also includes a number of additional lateral openings 265 therein which permit air and/or LVF to flow through the de-airing plug 264 in the opposite direction (i.e. to the right in FIGS. 12 and 13). This permits air to be used to push the diaphragm back into its starting position (i.e. that shown in FIG. 12), thereby allowing for the diaphragm 254 to be fully conformed to the sides of the proximal half 250 of the reservoir body by allowing the LVF to flow back out of the reservoir 214, through the inlet port 261, and this even when the tip of the diaphragm obstructs the central opening and passage of the de-airing plug 264. Accordingly, when the diaphragm is abutted against the proximal wall within the cavity 252 portion of the proximal half 250 of the reservoir, the diaphragm does not seal off the inlet before the first volume of the cavity 252 (i.e. that filed with LVF on the LVF side of the diaphragm) is maximally emptied. The lateral openings 265 may be comprised of a series of surface grooves and/or holes (4, 6, 12, or other number) which are arranged in a radially extending star formation and communicate with the central bore hole through the de-airing plug 264 in communication with the LVF inlet port 261. The de-airing plug 264 preferably includes a protruding hump portion which projects into the cavity 252 and within which the lateral openings 265 are provided.

As seen in FIG. 12, the cement reservoir 214 includes a cement side de-airing plug 270 which is disposed on the cement side of the reservoir, opposite the LVF side de-airing plug 264, in the distal half 253 of the reservoir body. The cement side de-airing plug 270 includes the bone cement outlet passage 272 therethrough, which is communication with the cannula when the bone cement reservoir 214 is connected therewith.

Figure 15:
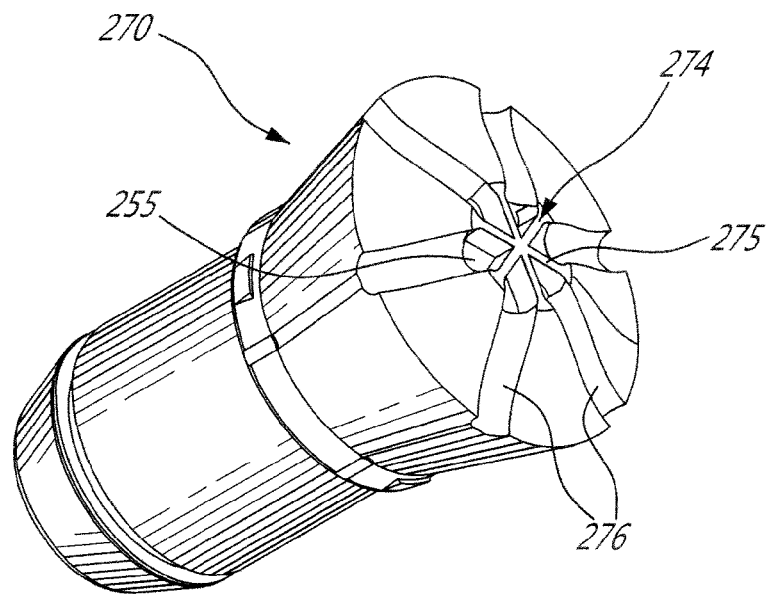
FIG. 15 is a perspective view of a cement-side de-airing plug portion of the bone cement reservoir of FIG. 12.

Referring to FIG. 15 showing the cement side de-airing plug 270 in more detail, a central proximally extending portion 274 extends into the cavity 252 and includes a number of star-shaped cross members 275 which extend over the opening to the central bone cement outlet passage 272. The protruding shape of the central portion 274 and the cross-shaped ribs 275 act as a positive stop for the diaphragm when it reaches its fully distended position (i.e. when the bone cement has been fully ejected from the bone cement reservoir 214. This helps to prevent the diaphragm from extruding into the bone cement outlet passage 272 in communication with the cannula, thereby preventing the possibility of rupture of the flexible diaphragm due to excessive stretching.

The cross-shaped ribs 275 extend across the outlet passage 272 of the cement reservoir act as a positive stop for the diaphragm and thus prevents the diaphragm from extruding into the cannula passage. These ribs and the outlet diameter are preferably designed to maintain a large total surface area of the openings through which the cement flows, but break up the total surface are into smaller areas, thus limiting the unsupported distance from point to point that the membrane with a thicker tip must bridge and support under pressure without rupturing.

Additionally, the cement side de-airing plug 270 includes a number of groves and/or passages 276 therein which communicate with the central opening 272 at the inlet thereof in the proximally protruding center portion 274. These groves and/or passages 276 prevent the fully distally distended diaphragm from centrally blocking the flow of the high viscosity material into the outlet. The grooves and/or holes 276 allow the cement to flow into the outlet 272, even when the central bore hole is covered/blocked by the distended diaphragm 254. The feature allows the high viscosity material in the second volume of the cavity 252 to be fully emptied into the outlet 272 of the bone cement reservoir 214, even when the diaphragm membrane does not distend in a symmetric manner.

The bone cement outlet passage 272 in the cement de-airing plug 270 of the bone cement reservoir 214 may be disposed in flow communication with the cannula by attaching a cannula directly to the bone cement reservoir 214 using a releasable locking mechanism. Preferably, the releasable locking mechanism will include a rotating element which permits relative rotation between the cannula and the bone cement reservoir. In other words, the outlet of the bone cement reservoir may have an integrated rotating element which permits a locking connection with the cannula. In this embodiment, the quick connect attachment members described above may not be required.

Figure 16:
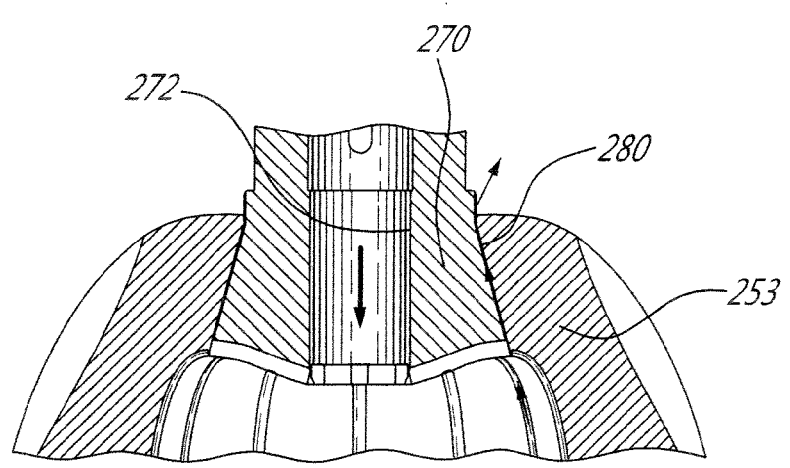
FIG. 16 is an enlarged cross-sectional view of the region "A" of FIG. 12.

Referring now to FIG. 16 showing the junction between the bone cement outlet de-airing plug 270 and the surrounding wall of the distal half 253 of the bone cement reservoir 214, very small diameter channels 280 are preferably provided at circumferentially spaced apart points about the frusto-conical mating surfaces of the cement outlet de-airing plug 270 and the distal reservoir half 253. These very small diameter channels 280 (for example of the order of 0.1 mm in diameter) allow for air in the cement reservoir to be evacuated during the cement filling process, however are too small to permit the much higher viscosity bone cement to escape from the cavity 252 of the bone cement reservoir, even under high pressures. Alternately, instead of using individually formed channels 280 to achieve this function, a single annular gap or passage of similarly small dimensions can be provided in lieu of the individual, circumferentially spaced apart channels. Alternately still, the two mating frusto-conical surfaces of the outlet plug 270 and the wall of the distal reservoir half 253 can be provided with a suitable surface roughness such as to allow air to vent from the cavity 252 while preventing bone cement from escaping therefrom.

The filling of high viscosity material into the reservoir 214 is performed through an extension tube 16 (see FIGS. 1-2 for example) in fluid communication with the second, bone cement side, volume of the cavity 252 within the bone cement reservoir 214. During filling of the cavity 252 in the reservoir 214 with bone cement, the extension tube is typically pointing upwards. The bone cement material ideally may have a moderately high viscosity only, so that it still can be poured into the cavity. When eventually injected into the bone cement reservoir 214 for filling purposes, the bone cement material preferably still has flow properties permitting the second volume within the cavity 252 to be filled "bottom up". When starting the filling procedure, the diaphragm membrane is preferably in the proximal position, fully abutted to the proximal wall of the cavity. It may also be in any other position. The second volume, before being filled with high viscosity material, is in communication with the environment and thus filled with air. It is in order to permit this air to vent when the second volume being filled with high viscosity material, that the series of small venting channels 280 are provided and, in at least one possible embodiment, arranged concentrically around the outlet of the reservoir. The venting channels 280 thereby establish a continuous communication between the second volume (bone cement side of the cavity 252) and the environment. The venting channels are typically around 0.1 mm (but can range from 0.01 mm to 0.5 mm) in diameter and extend the length of the reservoir full wall thickness (typically 2-10 mm, for example). The channels are therefore sized such as to easily vent any air at quite low pressures (typically below 0.2 MPa pressure) vent air, but even under very high pressures (ex: 10 MPa) are too small to permit the much more viscous bone cement material to escape the cavity 252 within the bone cement reservoir 214.

Although one is described above, several methods may be used to fill the cavity 52 of the bone cement reservoir with bone cement. A retrograde filling procedure may be used, for example, in which a cement mixing device is connected directly to a port in the closed egg-shaped bone cement reservoir 14, such as the outlet port 55 thereof for example, in order to charge a the cavity 52 full of bone cement. This greatly simplifies the filling procedure in comparison with existing systems, in which the bone cement must be mixed, transferred to an intermediate container and then charged into the injection device. In accordance with another embodiment, pre-filled bags of bone cement are provided and simply inserted directly into the reservoir 52 (i.e. the two halves 50 of the bone cement reservoir 14 are first opened and then re-sealed together), in a manner similar to pre-charged cartridges for example. This further simplifies the entire procedure, as no messy filling steps are required. Simply, a pre-filled bag of bone cement is introduced into one half of the open cavity 52, and the two halves 50 of the reservoir 14 are then closed together with the diaphragm 54 in place within the cavity, thereby sealing the bag of bone cement within the now enclosed cavity 52 of the reservoir. When the power piston is actuated to displace the LVF, the cement bag ruptures allowing the bone cement to flow out of the reservoir 14 and into the cannula 18.

The bone cement reservoir 14 may include a fill port 60 disposed in the top surface thereof, which can be used to fill the system, once connected together, with the low viscosity fluid. The fill port 60 helps minimize the time and skill required to fill the system with the low viscosity fluid and also helps to minimize air entrapment. However, the system may also be readily pre-filled with the LVF. The fill port 60 is, in at least the embodiment of FIG. 2, a check valve which allows the operator to fill the system with the LVF from the cement reservoir 14, through the extension tube 16 and back into the LVF reservoir 22 of the control handle 12, all while depressing the safety release button 46 on the control handle in order to open the check valve 44. In this way, if any small air bubbles should be present in the system (i.e. cement reservoir 14, extension tube 16 and control handle 12), they are forced into the LVF reservoir 22 where they will remain trapped without danger that they be drawn into the power piston and without the surgeon having to manipulate the device in any way. As a result, any air trapped in the LVF reservoir 22 can not be introduced back into the system.

As described above, the bone cement reservoir 14 is small, light and compact enough to be mounted directly to the top of the cannula 18. As such, the egg-shaped bone cement reservoir 14 is mounted to the upper handle portion 62 of the cannula 18 by a cement reservoir connector 64, to which the reservoir 14 is removably connected for example by a screw thread fitting 66 therebetween. The connector 64 is shaped such that the curved outer surface of the cement reservoir 14 is retained to the connector on one side thereof, and includes a second mating portion 65 which engages a corresponding opening in the upper surface of the handle 62 of the cannula 18.

Figure 6A:
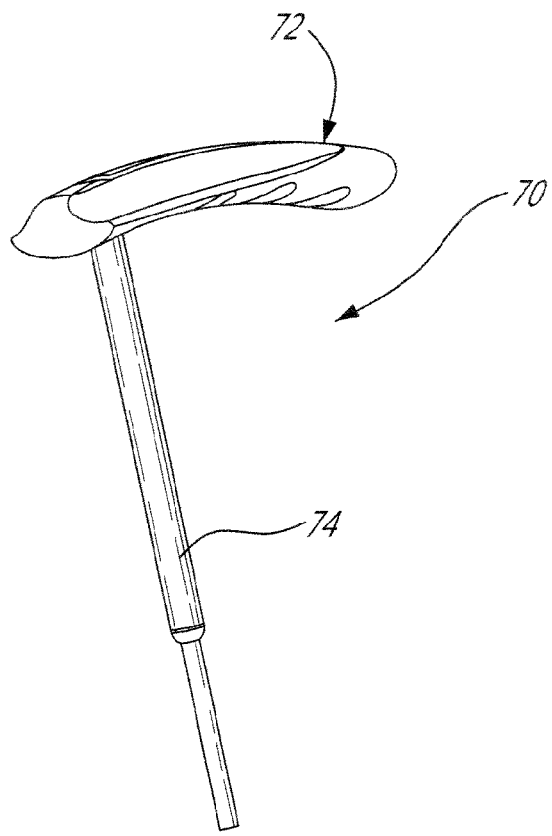
FIG. 6a is a perspective view of a cannula in accordance with one embodiment of the present invention.
Figure 6B:
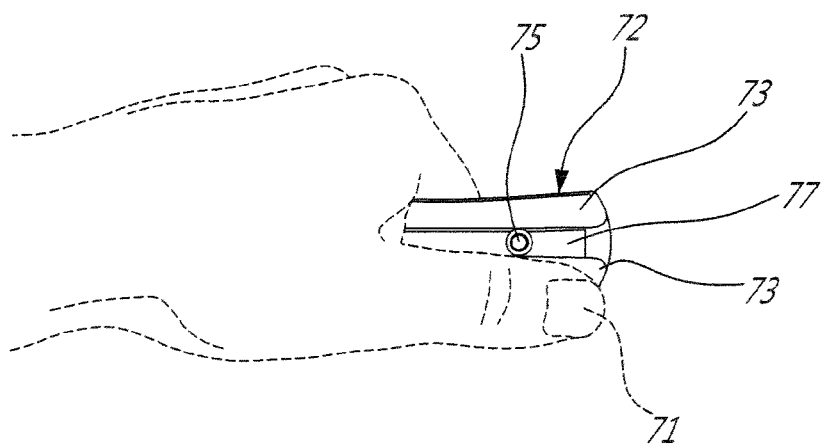
FIG. 6b is a top view of the cannula of FIG. 6a held by surgeon during use.

Referring now to FIGS. 6a-6b, a cannula 70 for use with the present bone cement injection system 10 includes a handle portion 72 and a tubular cannula body 74. Contrary to many known cannula designs, such as for example the cannula described in International Patent Application No. PCT/CA2005/000222 published on Aug. 25, 2005 as International Patent Application Publication No. WO 2005/077443, the contents of which is incorporated by reference, the handle 72 of the cannula 70 is of an improved design, both ergonomically and functionally. The cannula 70 was developed to address the existing problems with cannula placement within the vertebral body, in that the guiding K-wire inserted into the bone first and then used as guide to slide the cannula over it, is later pointing towards the surgeon's hand and/or palm. This hinders the surgeon's ability to readily manipulate the T-shaped handle. More specifically, the tubular body 74 is offset from the handle 72, or in other words the cannula body 74 is not located at a lateral mid-point on the handle as is the case with most T-shaped handles of the prior art. This gives a greater upper surface of the handle 72 which can be in contact with the surgeon's hand and/or palm, enabling a greater control of the cannula and therefore improved accuracy for its insertion into the vertebra. Further, the handle 72 is wider than that of a standard cannula of the prior art, which typically has a relatively narrower T-shaped handles. As seen in FIG. 6b, the wider handle 72 permits more room for the surgeon's thumb 71 to rest as close as possible to the upper opening 75 in the handle of the tubular cannula body 74. Specifically, lateral shelves 73 extend outward from the central body 77 of the handle 72 and are recessed from the raised central body portion 77, and along which the surgeon's thumb can rest in order to more accurately control the cannula 70 during its insertion within the vertebra. These lateral recessed shelves 73 also help reduce the risk of the guide wire piecing the surgeon's hand as the cannula is advanced over the guide wire and into the vertebral body. The design of the cannula 70 also reduces the likelihood of bending of the guide wire as the cannula is slid down over the guide wire, and thus prevents the inadvertent coupling of the cannula with the wire, which can lead to unwanted advancement of the guide wire within the patient. Finally, the design of the handle 72 allows the surgeon to maximize and control the force used to push and twist the cannula 70 down through the pedicle into the vertebra.

Another aspect of the present system is a method for determining a safe level of viscosity of the bone cement being injected using the bone cement injection system 10 and an indicator device for indicating when this desired level of viscosity has been reached. Injecting bone cement safely requires a delicate balance between the time required for injecting the cement along with a safe level of viscosity. If the cement is left to polymerize too long, resulting in the cement being too highly viscous, it will be more difficult to inject and also leave little remaining time before it cures for the surgeon to work with the cement if necessary. On the contrary, if the cement is injected at a low viscous state, the surgeon has ample time to perform the injection and make corrections but at the risk of the cement leaking from the vertebral body. As mentioned above, the known method previously used by surgeons is very qualitative, namely the surgeon employs a "glove test", where a sample of cement is taken from the injection device. If the bolus of cement sticks to the glove it is not ready. As this method is not overly reliable, the present system includes a method of determining when during the polymerization of the cement it is ready for injection to the bone element. This accordingly provides a more unbiased and controlled method for indicating the ideal starting point for injection of the bone cement.

Figure 9:
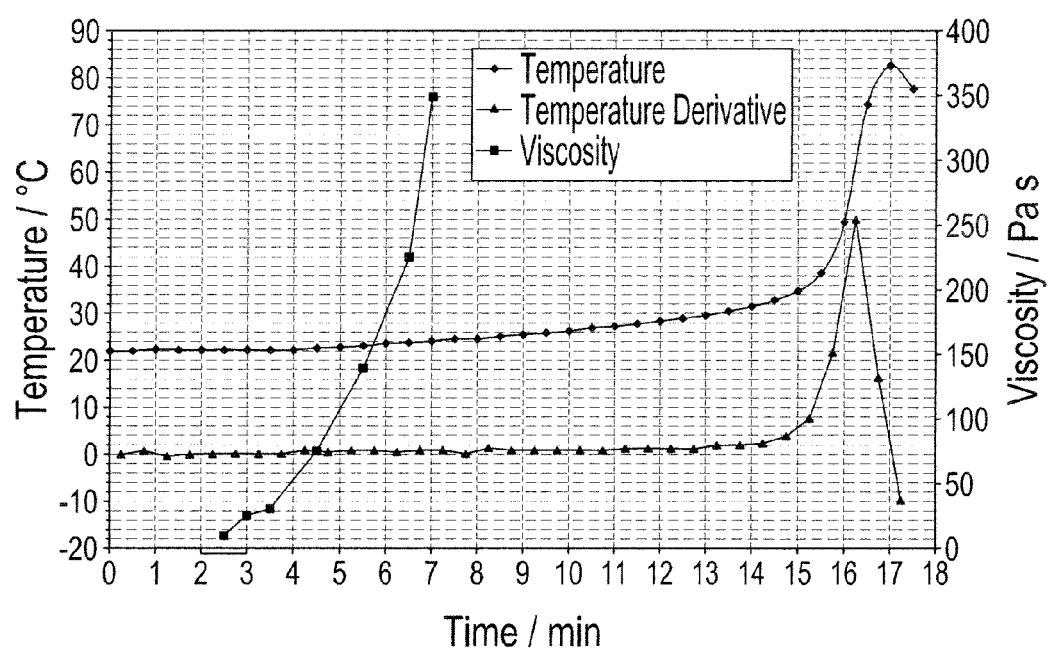
FIG. 9 is a graph depicting the effect of temperature and polymerization time on the viscosity of bone cement to be injected using the present bone cement injection system.

As seen in the graph of FIG. 9 which depicts test results of one particular example, a test was conducted in which the temperature and viscosity of a sample of PMMA bone cement were measured as the cement polymerized. The results of this test indicated that there is about a 1 to 2 degree Celsius change from the starting temperature of the cement to the time at which it is deemed to have a safe level of viscosity (i.e. greater than about 300 Pa*s) for injection. Accordingly, temperature was validated as an efficient and reliable indicator of the level of viscosity reached during the curing process of the bone cement. In view of this, the present system 10 may include a viscosity level indicator which includes, for example, a temperature sensor capable of measuring the temperature of the bone cement contained within the bone cement reservoir 14. The temperature sensor can include a thermocouple or a thermistor, for example. The viscosity level indicator thus comprises an electric circuit in electrical communication with the temperature sensor, such as to activate a visual or oral indicator, such as a light or warning sound for example, when the temperature reaches the predetermined level which corresponds to the desired viscosity level of the bone cement for injection. Accordingly, for example, an LED may be provided directly on the bone cement reservoir in communication with a temperature sensor within the cavity thereof, and the LED will turn from a red colour to a green colour when the desired viscosity of the bone cement is reached. This permits the surgeon therefore to be able to easily and accurately determine the desired temperature, and therefore viscosity level, of the bone cement which must be reached before injection begins. An alternate implementation of the means of identifying a desired temperature increase measured from the starting temperature, and therefore viscosity, of the bone cement is to include temperature sensitive crystals directly in the bone cement mixture itself or in an inner surface of the reservoir 14, such that when the bone cement mixture reaches a given temperature corresponding to a minimum viscosity level desired, the temperature sensitive crystals change colour thereby providing an accurate visual indication to the surgeon as to when to being injection of the bone cement.

The present bone cement injection system 10 can be disposable, and preferably uses a readily available hydraulic fluid, such as distilled water or saline solution for example, as the low viscosity fluid. Such fluids are available in ready supply in most hospitals supply rooms. Further, rather than having to fill the disposable device with the LVF, the LVF can be pre-charged or pre-filled within the LVF reservoir, thereby further simplifying the use of the present system by eliminating this filling step. The present system also permits a large amount of cement to be injected without requiring the removal of the device for refilling.

Although generally described above with respect to its use for injecting bone cement into a vertebra, it is to be understood that the present system 10 can also be used to inject other viscous materials into any existing cavity or virtual cavity, the latter being formed during injection. Generally, however, the present system 10 is used for the injection of a high viscosity material, for the purpose of either augmenting tissue or substituting tissue. Augmenting tissue results in more mechanical strength and more volume. Substituting tissue is carried out because of a loss of tissue due to a physiologic or pathologic process (e.g., age, degeneration, infection, trauma), or due to surgical removal. Therefore, while the main application of the present system 10 is for the injection of a relatively viscous bone cement into a vertebral body for augmentation, another possible use is the substitution of intervertebral disc tissue, more specifically the nucleus pulposus, with a viscous gel. Yet other applications are the injection of bone cement for mechanical augmentation into bones other than vertebrae, such as the femur, the metapyseal longbone areas around the knee, the distal radius, and others.

The above description is meant to be exemplary only, and one skilled in the art will recognize that changes may be made to the embodiments described without departure from the scope of the invention disclosed. Still other modifications that fall within the scope of the present invention will be apparent to those skilled in the art, in light of a review of this disclosure, and such modifications are intended to fall within the appended claims.

The invention claimed is:

1. A system for injecting an incompressible low viscosity fluid into a bone cement reservoir adapted to be engaged with a cannula through which a high viscosity bone cement is transferred from the bone cement reservoir to a bone element, the system comprising a control handle having a body, a grip portion at an outer end of the body and a central thumb-actuated power piston, the grip portion being configured for receiving at least two fingers a user such as to permit actuation of the control handle by the single hand of the user, the body including the power piston and a cylindrical low viscosity fluid reservoir concentrically disposed relative to each other, the low viscosity fluid reservoir containing the incompressible low viscosity fluid and the power piston having a power piston tube extending longitudinally through a center of the cylindrical low viscosity fluid reservoir such that the low viscosity fluid reservoir defines an annular shape and surrounds the power piston tube within the body, the power piston having a first plunger displaceable within the power piston tube, the annular low viscosity fluid reservoir containing a second plunger therein, the second plunger being annular and displaceable within the low viscosity fluid reservoir, the power piston tube having an inlet thereto in communication with the low viscosity fluid reservoir such that the low viscosity fluid in the low viscosity fluid reservoir is displaced by the second plunger out of the low viscosity fluid reservoir and into the power piston tube, and the power piston tube having an outlet through which the low viscosity fluid therein is expelled under pressure when the first plunger of the power piston is depressed by the thumb of the user.

2. The system as defined in claim 1, wherein the first plunger of the power piston is outwardly biased, such that a vacuum created within the power piston tube when the first plunger is released draws the second plunger in the low viscosity fluid reservoir towards the inlet of the power piston tube and forces the flow viscosity fluid from the low viscosity fluid reservoir into the power piston tube.

3. The system as defined in claim 2, wherein the first plunger of the power piston is outwardly biased by a spring, the spring being located entirely within the power piston tube.

4. The system as defined in claim 1, wherein the bone cement reservoir defines a substantially spherical cavity therein.

5. The system as defined in claim 4, wherein the spherical cavity is at least partially oblong.

6. The system as defined in claim 1, wherein the bone cement reservoir is remote from the control handle and connected thereto in fluid flow communication by an extension tube that is substantially non-compliant and which extends between the outlet of the power piston tube of the control handle and an inlet of the bone cement reservoir.

7. The system as defined in claim 4, wherein the bone cement reservoir has a substantially non-compliant body defining said cavity therein, and a diaphragm disposed within the cavity and separating the cavity into a low viscosity fluid receiving portion on one side thereof and a high viscosity fluid receiving portion on the opposite side thereof, the body of the bone cement reservoir comprising a proximal half and a distal half sealingly fastened together at a midpoint of the bone cement reservoir, and the diaphragm having an outer periphery fastened between the proximal half and distal half at said midpoint of the bone cement reservoir.

8. The system as defined in claim 7, wherein the diaphragm is displaced between a loaded position and a dispensed position thereof within said cavity by inverting itself, such that the diagraph assumes a substantially hemispherical concave shape in both the loaded position and the dispensed position.

9. The system as defined in claim 8, wherein the low viscosity fluid receiving portion being in fluid communication with said inlet to the bone cement reservoir and the high viscosity fluid receiving portion being in fluid communication with an outlet of the bone cement reservoir, the diaphragm being displaceable by the low viscosity fluid when injected therein by the control handle between the loaded position, wherein the diaphragm is proximate a proximal end wall of the cavity and the high viscosity fluid receiving portion occupies a majority of the cavity, and the dispensed position, wherein the diaphragm is displaced towards the distal end wall of the cavity and the low viscosity fluid receiving portion occupies the majority of the cavity, whereby the diaphragm acts as a material-moving membrane which is displaced by the low viscosity fluid acting thereagainst to force the high viscosity material on the opposite side of the diaphragm out of said cavity, via said outlet of the bone cement reservoir.

10. The system as defined in claim 4, wherein opposed proximal and distal end walls of said cavity of the bone cement reservoir each have a hemispherical concave shape.

11. The system as defined in claim 1, wherein the bone cement reservoir comprises a body comprised of a proximal half including the inlet to the bone cement reservoir and a distal half including the outlet from the bone cement reservoir, the proximal and distal halves being sealingly fastened together to enclose said cavity therewithin, the proximal half being mating received within a corresponding opening in the distal half such that an annular wall portion of the distal half surrounds the proximal half.

12. The system as defined in claim 11, wherein one or more sealing elements are radially disposed between an outer circumferential wall of the proximal half of the bone cement reservoir body and the annular wall portion of the distal half.

13. The system as defined in claim 12, wherein an outer periphery of the diagraph provides a seal between the proximal and distal halves of the bone cement reservoir body when fastened together.

14. The system as defined in claim 13, wherein a proximally located nut which surrounds the proximal half of the proximal half releasably fastens the proximal and distal halves of the bone cement reservoir body together.

15. The system as defined in claim 1, wherein the power piston of the control handle includes a pressure relief mechanism for equalizing pressure in the power piston, thereby removing force acting on the low viscosity fluid by the power piston and immediately stopping further displacement of the low viscosity fluid through the system, the pressure relief mechanism including a pressure relief valve in communication with the outlet of the power piston for equalizing the pressure therein with atmospheric pressure when the pressure relief valve is actuated, a pressure relief button in proximity of the grip portion, and a safety pressure relief tube which is concentric with the power piston tube and is longitudinally displaceable relative thereto, the safety pressure relief tube interconnecting the pressure relief button and the pressure relief valve at opposite ends of the control handle.

16. The system as defined in claim 15, wherein the pressure relief button is an annular button that is concentric with, and which surrounds, the first plunger and the power piston.

17. The system as defined in claim 15, wherein the pressure relief mechanism includes one or more sealing elements integrally provided within the power piston, the sealing elements having a predetermined pressure threshold selected to be greater than a normal maximum pressure of the low viscosity fluid required for cement injection but less than a predetermined pressure at which mechanical integrity of components of the system are compromised, whereby the sealing elements are designed to intentionally but temporarily leak when the pressure of the low viscosity fluid is greater than said normal maximum pressure.

18. The system as defined in claim 1, wherein one way advancement of the low viscosity fluid out of the control handle, when the first plunger of the power piston is depressed by the user, is achieved using a check valve assembly comprising at least two check valves, the two check valves being substantially linearly arranged and including a check valve plug that is integrated directly into a tip of the first plunger of the power piston, the check valve plug closes when the first plunger is depressed, thereby forcing the low viscosity fluid out of the power piston, but opens when the first plunger moves outwardly in the opposite direction.

19. A system for injecting a high viscosity bone cement into a cannula for delivery to a bone element, comprising:
a control handle configured for actuation by a single hand of a user, the control handle having a cylindrical body having a power piston and a low viscosity fluid reservoir concentrically disposed relative to each other, the low viscosity fluid reservoir containing an incompressible low viscosity fluid and the power piston having a power piston tube extending longitudinally through a center of the low viscosity fluid reservoir such that the low viscosity fluid reservoir defines an annular shape and surrounds the power piston tube within the body, the power piston having a first plunger displaceable within the power piston tube, the annular low viscosity fluid reservoir containing a second plunger therein, the second plunger being annular and displaceable within the low viscosity fluid reservoir, the first and second plungers being concentric and displaceable one within the other, the power piston having an inlet thereto in communication with the low viscosity fluid reservoir such that the low viscosity fluid is displaced by the second plunger out of the low viscosity fluid reservoir and into the power piston tube, and an outlet through which the low viscosity fluid is expelled when the first plunger of the power piston is depressed by the user; and
a bone cement reservoir containing the high viscosity bone cement, the bone cement reservoir being remote from the control handle and connected thereto in fluid flow communication by an extension tube, having an inlet connected in fluid flow communication with the outlet of the power piston of the control handle and an outlet adapted to communicate with the cannula for transferring the high viscosity material thereto, the second reservoir having a non-compliant body defining a cavity therein, a diaphragm disposed within the cavity and having an outer periphery thereof fixed to the body, the diaphragm separating said cavity into a low viscosity fluid receiving portion on one side thereof and a high viscosity fluid receiving portion on the opposite side thereof, the low viscosity fluid receiving portion being in fluid communication with said inlet to the second reservoir and the high viscosity fluid receiving portion being in fluid communication with said outlet of the second reservoir, the diaphragm having a shape corresponding to opposed proximal and distal end walls of said cavity, the diaphragm being displaceable by the low viscosity fluid between a loaded position, wherein the diaphragm is abutted against the proximal end wall and the cavity is filled with said high viscosity material, and a dispensed position, wherein the diaphragm displaced towards the distal end wall and the cavity is at least partially filled with said low viscosity fluid, the diaphragm thereby being a material-moving membrane which is displaced by the low viscosity fluid acting thereagainst to force the high viscosity material on the opposite side of the diaphragm out of said cavity, via said outlet of the second reservoir, and into the cannula.

20. The system as defined in claim 19, wherein the cavity of the bone cement reservoir defines a shape that is symmetrical about a central, transversely extending plane.

21. The system as defined in claim 19, wherein the opposed proximal and distal end walls of said cavity define a hemispherical concave shape.

22. The system as defined in claim 19, wherein the cavity of the bone cement reservoir is substantially oblong, having a cylindrical middle section which interconnects the opposed proximal and distal end walls which have a hemispherical concave shape.

23. The system as defined in claim 22, wherein the diaphragm has a substantially hemispherical shape corresponding to the proximal and distal end walls of said cavity.

24. The system as defined in claim 19, wherein the outer periphery of the diaphragm is fixed to the body of the bone cement reservoir at a midpoint between said proximal and distal end walls of the cavity.

25. The system as defined in claim 19, wherein the body of the bone cement reservoir comprises a first half and a second half removably fastened together to enclose said cavity, the outer periphery of the diagraph having providing a seal between the first half and the second half of the body when fastened together.

26. The system as defined in claim 19, wherein a non-compliant extension tube extends between the control handle and the bone cement reservoir.

27. The system as defined in claim 26, wherein the extension tube is removably engaged with the bone cement reservoir and the control handle.

28. The system as defined in claim 19, wherein the bone cement reservoir is configured for mounting directly to the cannula.

29. The system as defined in claim 19, wherein the power piston includes a safety relief valve for equalizing pressure in the power piston tube, the safety relief valve is in fluid communication with the outlet of the power piston tube for equalizing the pressure therein with atmospheric pressure when the pressure relief valve is activated, thereby removing force acting on the low viscosity fluid by the power piston and immediately stopping further displacement of the low viscosity fluid through the system, wherein the safety relief valve is actuated by a safety pressure relief tube which is concentric with the power piston tube and is longitudinally displaceable relative thereto.

30. The system as defined in claim 29, wherein a pressure relief button disposed proximate the grip portion actuates the safety pressure relief tube for displacement thereof, the pressure relief button being annular and surrounding the first plunger of the power piston.

31. The system as defined in claim 19, wherein the low viscosity fluid receiving portion defines a first volume and the high viscosity fluid receiving portion defines a second volume, and wherein movement of the diaphragm varies the first and second volumes inversely proportionally.

32. The system as defined in claim 19, wherein the diaphragm is flexible and substantially non-compliant.

33. The system as defined in claim 19, wherein the diaphragm includes a central tip portion which has a greater thickness than that of a remainder of the diaphragm.

34. A system for injecting a high viscosity bone cement into a bone element, comprising:
   a bone cement reservoir for storing the high viscosity bone cement prior to injection thereof, the reservoir having a substantially non-compliant body defining a cavity therein, and including an inlet and outlet to said cavity, a material-moving membrane separating the cavity into a first portion having a first volume adapted to receive an incompressible low viscosity fluid via said inlet to said cavity and a second portion having a second volume adapted to receive the high viscosity bone cement, the material-moving membrane being flexible such as to corresponding to opposed proximal and distal end walls of said cavity, the material-moving membrane being displaceable by the low viscosity fluid between a loaded position, wherein the material-moving membrane is abutted against the proximal end wall and the cavity contains only said high viscosity bone cement therein, and a dispensed position, wherein the diaphragm is displaced towards the distal end wall by the low viscosity fluid, the material-moving membrane thereby varying the first and second volumes inversely proportionally; and
   a fluid injector connected in fluid flow communication with the inlet of the cavity, the fluid injector being actuable to displace the incompressible low viscosity fluid into the first portion of said cavity in order to displace the material-moving membrane therein to increase the first volume and decrease the second volume, thereby ejecting the high viscosity bone cement out of the body via the outlet of the cavity, the fluid injector having a low viscosity fluid reservoir and an integral power piston for displacing the low viscosity fluid, the power piston being disposed concentrically within the low viscosity fluid reservoir such that the low viscosity fluid reservoir defines an annular bore surrounding the power piston, the power piston having a first plunger therein and the low viscosity fluid reservoir having a second plunger therein.

35. The system as defined in claim 34, wherein the fluid injector includes a control handle configured for actuation by a single hand of a user, the fluid injector having closed finger loops configured to receive at least two fingers of a user's hand, thereby permitting the control handle to be at least one of rotated, inclined away from a vertical orientation and inverted.

36. The system as defined in claim 34, wherein the second plunger within the low viscosity fluid reservoir is annular and is displaced therewithin as the level of low viscosity fluid changes, the second plunger acting as a liquid level guide which permits accurate determination of the quantity of low viscosity fluid injected out of the fluid injector and therefore the quantity of the high viscosity bone cement that is ejected from the outlet of the high viscosity fluid reservoir cavity.

37. The system as defined in claim 34, wherein a body of said reservoir comprises a first half and a second half removably fastened together to enclose said cavity, the outer periphery of the material-moving membrane being engaged between the first half and the second half of the reservoir body and providing a seal therebetween when fastened together.

38. The system as defined in claim 34, wherein the cavity of the reservoir defines a shape that is symmetrical about a central, transversely extending plane.

39. The system as defined in claim 34, wherein the opposed proximal and distal end walls of said cavity define a hemispherical concave shape.

40. The system as defined in claim 39, wherein the material-moving membrane has a substantially hemispherical shape corresponding to the proximal and distal end walls of said cavity.

41. The system as defined in claim 34, wherein the cavity is substantially oblong, having a cylindrical middle section which interconnects the opposed proximal and distal end walls which have a hemispherical concave shape.

42. The system as defined in claim 34, wherein a viscosity level indicator in heat transfer communication with at least a portion of the cavity within said reservoir, the viscosity level indicator including a temperature sensor which continuously measures a temperature of the high viscosity fluid contained in said cavity, and an indicator element in electrical communication with said temperature sensor for indicating when the measured temperature reaches a predetermined rate of increase indicating that a threshold polymerization time of the high viscosity bone cement has been reached, said threshold polymerization time corresponding to a selected viscosity level that is suitable for injection of the high viscosity bone cement.

* * * * *